United States Patent
Kantorovich

(12) 
(10) Patent No.: US 6,261,233 B1
(45) Date of Patent: Jul. 17, 2001

(54) METHOD AND DEVICE FOR A BLOOD VELOCITY DETERMINATION

(75) Inventor: Edward Kantorovich, Rehovot (IL)

(73) Assignee: Sunlight Medical Ltd., Rehovot (IL)

( * ) Notice: Subject to any disclaimer, the term of this patent is extended or adjusted under 35 U.S.C. 154(b) by 0 days.

(21) Appl. No.: 09/101,149
(22) PCT Filed: Jan. 3, 1997
(86) PCT No.: PCT/IL97/00004
   § 371 Date: Jul. 1, 1998
   § 102(e) Date: Jul. 1, 1998
(87) PCT Pub. No.: WO97/24986
   PCT Pub. Date: Jul. 17, 1997

Related U.S. Application Data

(60) Provisional application No. 60/009,670, filed on Jan. 5, 1996.

(51) Int. Cl.[7] ................................................. A61B 8/06
(52) U.S. Cl. ................................................. 600/454
(58) Field of Search ........................... 600/454–456; 73/861.25, 861.28, 19.03, 19.07; 367/100, 89–90

(56) References Cited

U.S. PATENT DOCUMENTS

| | | | |
|---|---|---|---|
| 3,987,673 | 10/1976 | Hansen | 73/194 |
| 4,370,985 | 2/1983 | Takeichi et al. | 128/663 |
| 4,476,874 | 10/1984 | Taenzer et al. | 128/663 |
| 5,119,821 | 6/1992 | Tuchler | 128/664.04 |
| 5,406,854 | 4/1995 | Wagner | 73/861.25 |
| 5,409,010 | 4/1995 | Beach et al. | 128/661.09 |
| 5,488,953 | 2/1996 | Vilkomerson | 128/661.8 |
| 5,562,098 | * 10/1996 | Levver | 600/454 |

FOREIGN PATENT DOCUMENTS

| | | |
|---|---|---|
| 0 538 885 | 4/1993 | (EP) . |
| 2 016 998 | 5/1970 | (FR) . |
| 1 238 585 | 7/1971 | (GB) . |

OTHER PUBLICATIONS

Powalowski T., "Ultrasonic System for Noninvasive Measurement of Hemodynamic Parameters of Human Arterial–Vascular System", *Archives of Acoustics*, vol. 13, Issue 1–2, 1988, p. 89–108.

Powalowski T., "A Noninvasive Method for Vascular input impedance Determination Applied in Diagnostics of the Carotid Arteries", *Archives of Acoustics*, vol. 14, Issues 3–4, 1989, p. 293–312.

Overbeck et al., "Vector Doppler: Accurate Measurement of Blood Velocity in Two Dimensions", *Ultrasound in Medicine and Biology*, vol. 13, No. 1, Pergamon Press, 1992, pp. 19–31.

J.P. Woodcock, "The Transcutaneous Ultrasonic Flow–Velocity Meter in the Study of Arterial Blood Velocity", *Proceedings of the Conference on Ultrasonics in Biology and Medicine*, UBIMED–70, Jablonna–Warsaw, Oct. 5–10, 1970.

(List continued on next page.)

Primary Examiner—Francis J. Jaworski
(74) Attorney, Agent, or Firm—Kenyon & Kenyon

(57) ABSTRACT

A method of determining the velocity of a flowing material, suspended in a liquid and flowing in a conduit, including irradiating the conduit with ultrasonic waves, detecting first Doppler-shifted reflections of the waves from the material, which first reflections have a positive Doppler-shift, and detecting second Doppler shifted reflections of the waves from the material, which second reflections have a negative Doppler-shift. The flow velocity is estimated based on the extent of the positive and negative Doppler-shifts. The first and second reflections may be summed to form a composite signal and the range of Doppler-shifts in the composite signal is used to estimate the flow velocity.

23 Claims, 26 Drawing Sheets-

OTHER PUBLICATIONS

J.P. Wood, "The Significance of Changes in the Velocity/Time Waveform in Occlusive Arterial Disease of the Leg", *Proceedings of the Conference on Ultrasonics in Biology and Medicine*, UBIMED–70, Jablonna–Warsaw, Oct. 5–10, 1970.

Christman et al., "In vivo microbubble detection in decompression sickness using a second harmonic resonant bubble detector", Undersea Biomedical Research, vol. 13, No. 1, pp. 1–18, 1986.

M.P. Spencer, "Safe Decompression With the Doppler Ultrasonic Blood Bubble Detector", Proceedings of the Fifth Symposium on Underwater Physiology, FASEB, Bethesda, Maryland, 1976, pp. 311–325.

Powell et al., "The Pathophysiology of Decompression Sickness and the Effects of Doppler Detectable Bubbles", Technical Report O.N.R. Contract N00014–73–C–0094, Institute of Applied Physiology and Medicine, Seattle, WA 98122.

Shahar Kol et al., "The Potential Role of Oxygen in the Prevention of Neurologic Deficits After Cardiac Surgery", Intensive and Critical Care Digest, vol. 12, No. 4, Dec. 4, 1993 pp. 48–50.

Shahar Kol et al., "Hyperbaric Oxygenation for Arterial Air Embolism During Cardiopulmonary Bypass", Ann. Thorac. Surg, vol. 55, 1993, pp. 401–503.

G.H. Adkisson et al., "Cerebral Perfusion Deficits in Disbarric Illness", The Lancet, Jul. 15, 1989, pp. 19–121.

G. Avvisati et al., Tranexamic Acid for Control of Haemorrhage in Acute Promyelocytic Leukemia , The Lancet, Saturday, Jul. 15, 1989, p. 11.

Y. Melamed et al., "Medical Problems Associated With Underwater Diving", The New England Journal of Medicine, vol. 326, No. 1, 1992, pp. 30–35.

R. Smith et al., "Elevation of Serum Creatine Kinase in Divers with Arterial Gas Embolization" New England Journal of Medicine, vol. 330, No. 1, 1994, pp. 19–24.

A. Hope et al., "Intravascular Gas Bubble Detection by Doppler Ultrasound in Conscious Rats", Proceedings of the XIXth Annual Meeting of EUBS 1993, Trondheim, Norway, p. 273.

M.R. Powell et al., "Ultrasonic Surveillance of Decompression", "The Physiology of Medicine of Diving", Third Edition, Ed. Best Publishing Co., San Pedro, California, pp. 404–434.

* cited by examiner

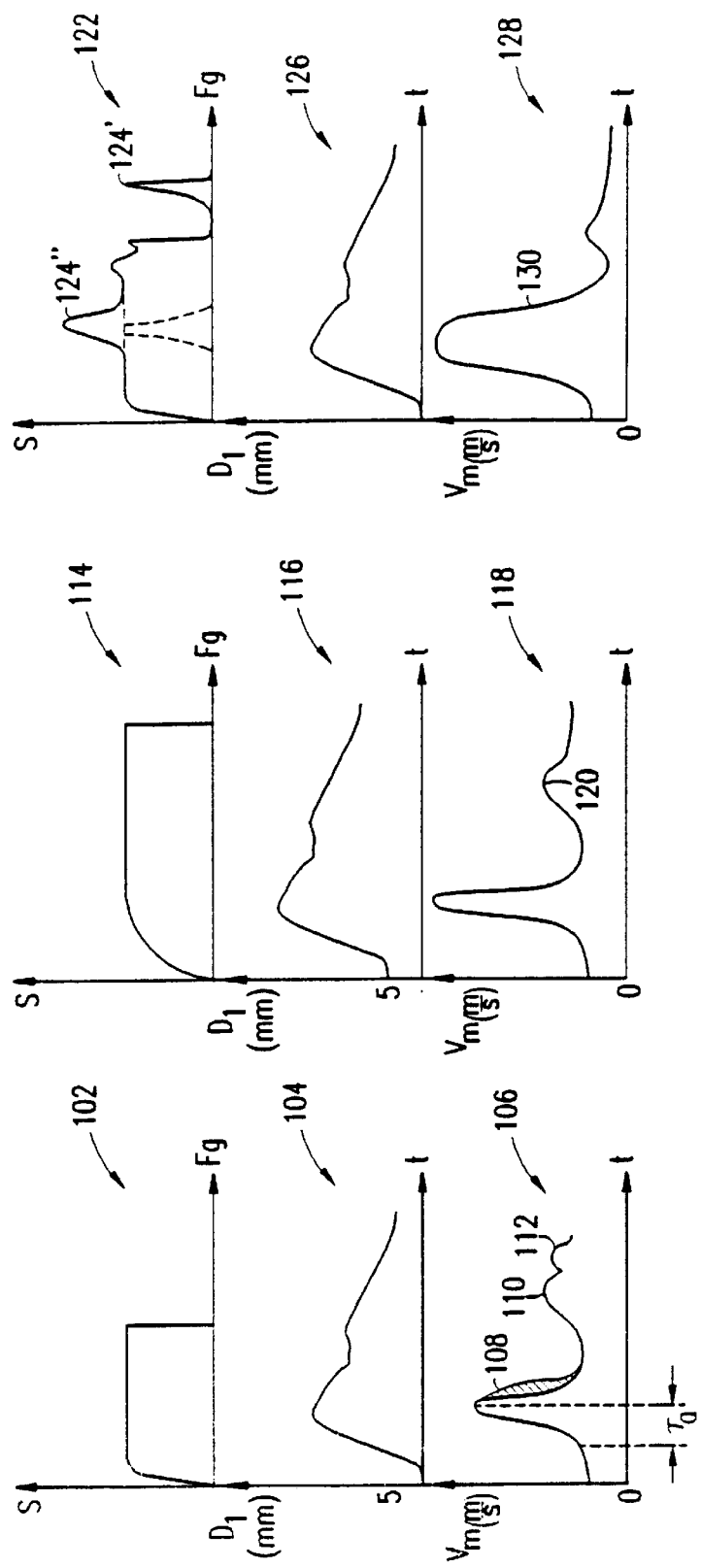

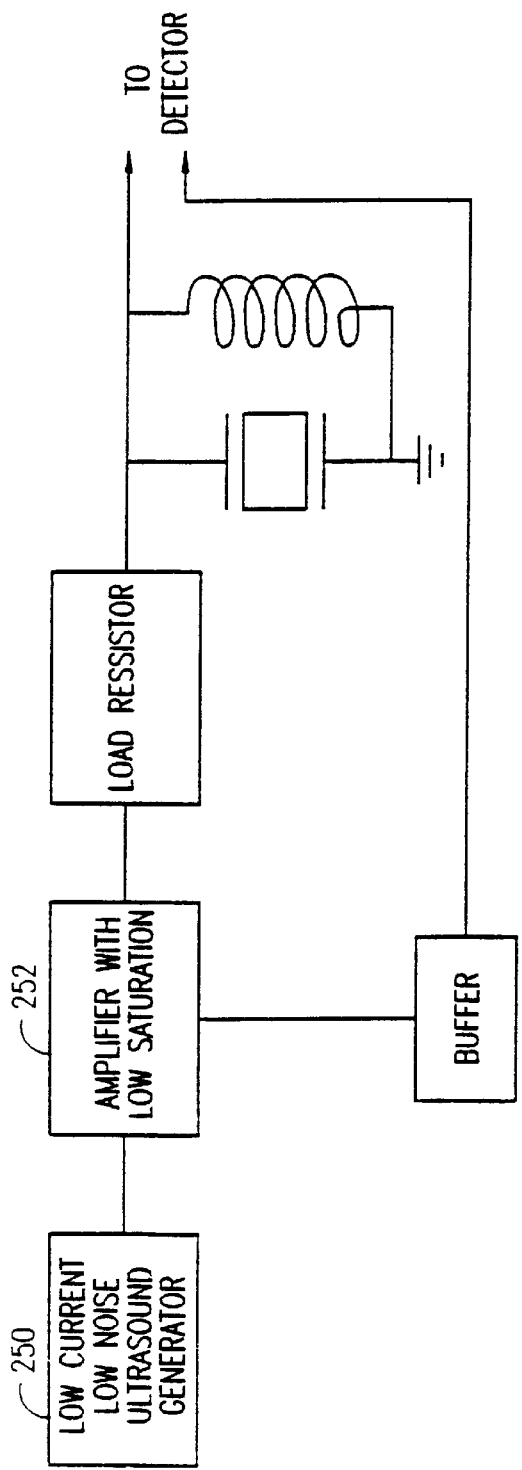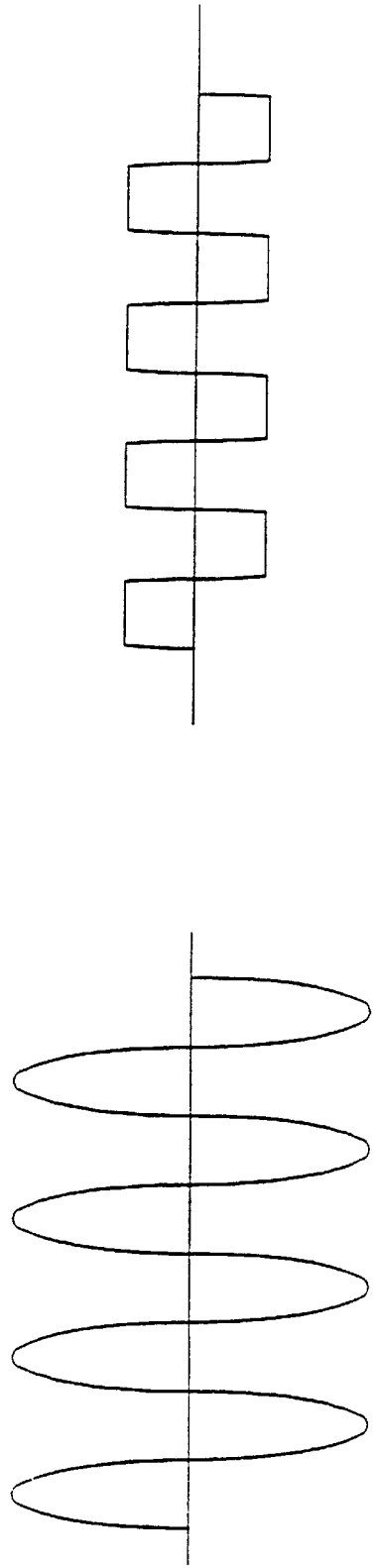
FIG. 14A
FIG. 14B
FIG. 14C

METHOD AND DEVICE FOR A BLOOD VELOCITY DETERMINATION

RELATED APPLICATIONS

This application is a national stage filing under 35 U.S.C. § 371 of PCT International Application No. PCT/IL97/00004, filed Jan. 3, 1997, which claims the benefit of U.S. Provisional Application No. 60/009,670, filed Jan. 5, 1996.

FIELD OF THE INVENTION

The present invention relates to apparatus and methods for non-invasive measurement of parameters of the cardio-vascular system, such as local blood flow volume, blood pressure and detection of gas bubbles in the blood.

BACKGROUND OF THE INVENTION

One of the important physiological systems in the human body is the cardiovascular system, which includes the heart, the arterial system and the venous system. Many imaging modalities can be used to investigate the structural properties of the cardio-vascular system, including, angiography, X-ray CT, MRI, SPECT and ultrasound. However, it is difficult to non-invasivly determine haemodynamic properties of the cardiovascular system. Determining the following haemodynamic properties is particularly useful:

(a) blood flow volume in a particular arterial/venous subsystem;

(b) local turbulence and pressure drops, which may indicate stenoses and/or aneurysms;

(c) pulse wave velocity;

(d) cardiac left ventricular stroke volume; and (e) the reaction of arteries and veins to a pulse wave.

Doppler ultrasound imaging is widely used to determine local blood velocity flow in arteries. The frequency shift $\Delta f$ of an ultrasonic wave of wavelength X, which impinges particles moving at a velocity v, is given by the following equation:

$$\Delta f = \frac{2*v}{\lambda}[\cos(\alpha) + \cos(\beta)] \quad (1)$$

In the case of blood, the ultrasonic wave is reflected mainly from red blood cells, which move in the same direction as the blood flow. It is relatively straightforward to transmit a wave of a known wavelength to a blood vessel, detect a reflected wave and determine the velocity of the blood based on equation (1). However, the magnitude of the frequency shift $\Delta f$ is affected not only by the blood velocity v but also by an angle of incidence $\alpha$ and a reflectance angle $\beta$ of the wave from the blood. Typically in prior art measurements, these angles are not definitely determined, leading to an error of over 15% in velocity determination, as will be shown below with reference to FIG. 2.

One known method of more precisely determining the angle of incidence $\alpha$ and the reflectance angle $\beta$ is to generate an ultrasonic image including the blood vessel. The angles $\alpha$ and $\beta$ are measured on the image along an imaging beam which is used for Doppler frequency shift determination. However, due to limitations of the ultrasonic imaging modality, the angle determination is not sufficiently precise and a significant error in velocity determination can be expected. In addition, the price and complexity of an ultrasonic imaging system are much higher than that of a simple Doppler-ultrasound system.

There also exist many invasive methods for determining haemodynamic properties. One method includes inserting a sensor carrying catheter into a vein or artery. Haemodynamic properties, such as pressure or velocity, are very precisely sensed by the sensor and are converted into a host of dependent properties, such as blood vessel impedance.

Another, less invasive, method is magnetic flow determination. In this method, a coil is placed around an intact blood vessel. A magnetic field is induced in the coil. Since blood is a conductor, the flow of blood in the magnetic filed induces a voltage across the blood vessel which is proportional to the flow.

There is however a need for a precise, non-invasive method for determining blood velocity and other haemodynamic properties.

Blood velocity determination and detection of small gas bubbles in the blood are related, since encapsulated gas bubbles are readily detectable using Doppler-ultrasound. Gas bubbles do not naturally occur in the vascular system. Certain medical procedures, such as CPB (cardiopulmonary bypass), and certain types of physical trauma, may infuse air bubbles into the vascular system. In addition, certain activities, most notably sea-diving, can cause the creation of air bubbles in the vascular system. In general, gas bubbles cause severe and lasting neurological effects, as well as other grievous bodily damage. However, it is relatively difficult to monitor the formation of gas bubbles in vivo. As a result, sea-divers use non-personalized diving tables which estimate the danger from gas bubbles in the divers blood.

As mentioned above, Doppler-ultrasound can be used to detect gas bubbles, however, the current state of the art does not provide means sensitive enough to detect small, yet damaging, gas bubbles in the blood. In addition, there is no commercially available simple apparatus for monitoring of gas bubbles in sea-divers.

Gas bubbles can also be detected, counted and monitored under a microscope., however, this type of monitoring is generally not practical even for medical situations, as well as being extremely invasive.

Blood pressure is usually determined using a pressure cuff on the brachial artery in the arm. This method has a relatively low precision and only measures the systolic and diastolic pressures. In "Ultrasonic System for Noninvasive Measurement of Hemodynamic Parameters of Human Arterial-Vascular System", by Powalowski T., *Archives Of Acoustics*, Vol. 13, Issue 1-2, p. 89–108 (1988) and in "A Noninvasive Ultrasonic Method for Vascular Input Impedance Determination Applied in Diagnosis of the Carotid Arteries", by Powaiowski T., *Archives Of Acoustics*, Vol. 14, Issue 3-4, p. 293–312 (1989), the disclosures of which are incorporated herein by reference, a method of estimating instantaneous blood pressure in a blood vessel is described. However, Powalowski's estimation method has at least two limitations. First, estimating the instantaneous blood pressure requires determining the diastolic and systolic blood pressures using a pressure cuff Second, the method used for determining the velocity of the blood flow in the blood vessel is not very precise.

U.S. Pat. No. 5,488,953 to Vilkomerson, the disclosure of which is incorporated herein by reference, describes a method and a device for measuring the flow velocity in a blood vessel using ultrasonic Doppler processing, independent of an orientation of the device. However, the method described in the '953 patent requires that the angles between a plurality of ultrasonic beams and the flow be determined.

An article titled "Vector Doppler: Accurate Measurement of Blood Velocity in Two Dimensions," by John R. Overbeck. Kirk W. Beach and D. Eugene Strandness, Jr., *Ultrasound in Medicine and Biology*, Vol. 13, No. 1, pp. 19–31, printed by Pergamon press, USA, 1992, and which is incorporated herein by reference describes several multi-transducer Doppler ultrasound devices, in which the angle of incidence is determined by analyzing the difference in Doppler spectra of different transducers.

U.S. Pat. No. 5,406,854, the disclosure of which is incorporated herein by reference, describes a Doppler flowmeter in which signals from several receivers, all of which are similarly oriented to the flow, are mixed to increase the system sensitivity.

U.S. Pat. No. 5,119,821, the disclosure of which is incorporated herein by reference, describes an ultrasonic probe having two probes oriented at about 45 degrees to each other. By comparing the signals received by the two probes from a blood flow, constrictions in the flow can be determined.

Woodcock, J. P., "The Transcutaneous Ultrasonic Flow-Velocity Meter in the Study of Arterial Blood Velocity," *Proceedings of the Conference on Ultrasonics in Biology and Medicine*, UBIMED-70, Jablonna-Warsaw, Oct. 5–10, 1970, the disclosure of which is incorporated herein by reference, describes the use of two simultaneous measurements of flow parameters to ascertain the condition of corollary blood vessels.

SUMMARY OF THE INVENTION

It is an object of some embodiments of the present invention to provide apparatus and methods for precise determination of various haemodynamic parameters of the cardiovascular system, including at least one of:

(a) blood velocity;

(b) blood flow rate;

(c) pulse wave velocity;

(d) vessel dilation;

(e) dynamic vessel radius and/or cross-section;

(f) turbulence;

(g) estimate of stenosis percentage; and (h) blood pressure.

Further, it is an object of some embodiments of the present invention to provide means for measuring local haemodynamic values as a function of time and/or as a function of the locale of the measurement. For example, comparing the flow rate in an artery to the flow rate in each of a plurality of branches emanating from the artery. Another example is determining the pressure drop along an artery which is caused by stenosis.

It is a further object of some embodiments of the present invention to provide a non-invasive, simple to operate apparatus which is operative to precisely determine a wide range of haemodynamic properties of the cardiovascular system.

Another object of some embodiments of the present invention is to provide methods and apparatus for determining the haemodynamic properties of arteries and/or veins, particularly at the extremities of a body. Preferably, significant portions of the vascular system are mapped using methods and apparatus of the present invention.

An object of some embodiments of the present invention is to provide ultrasonic measurement methods and/or apparatus which can be easily integrated with existing ultrasonic equipment, particularly ultrasonic imaging systems.

It is an object of some embodiments of the present invention to provide a method for detecting small gas bubbles in vivo, or example, bubbles smaller than 5 $\mu$. It is an additional object of some embodiments of the present invention to provide a simple apparatus for detecting and monitoring as bubbles in vivo, such as would be useful for sea-divers. Detecting and monitoring gas bubbles in blood is also useful in hyperbaric medical procedures. An additional embodiment of the invention provides apparatus for monitoring the formation of gas bubbles in medical blood circulating devices such as CPB.

In a preferred embodiment of the present invention, a Doppler spectrum of a blood flow in response to a first ultrasound beam is combined with a Doppler spectrum of the blood flow in response to a second ultrasound beam to yield a higher quality Doppler spectrum. The first and second beams have different beam directions. One beam preferably has a direction component in the general direction of the flow and the other beam preferably has a direction component in the general direction opposite the flow. Preferably, the Doppler spectra are acquired substantially simultaneously. The combined Doppler spectrum is then analyzed to determine haemodynamic properties of the flow, such as flow velocity. It should be appreciated that the quality of the combined Doppler spectrum is significantly higher than typical in the prior art, so more precise information can be extracted therefrom.

In a further preferred embodiment of the invention, more than two Doppler spectra are combined. The spectra may be reflections of co-planar ultrasound beams, or of beams which are not co-planar.

In a preferred embodiment of the invention, particularly suitable for estimating left ventricular stroke volume, the Doppler spectra from three, non-parallel, beams are analyzed to determine their incidence angle on the aorta and they are combined to form a combined Doppler spectrum. A precise estimate of the flow velocity in the aorta is determined from the combined spectrum, and, based on the diameter of the aorta, the amount of blood flowing through the aorta can be estimated. The left ventricle stroke volume is equal to the amount of blood flowing in the aorta during one heart beat. Preferably, the diameter of the aorta is measured using an ultrasonic device substantially simultaneously with the Doppler measurement. Alternatively, the diameter of the aorta is determined from the Doppler spectrum. For example, very short pulses can be used and the inner diameter of the aorta is determined from the time extent of Doppler shifted reflections of the short pulse. Since the diameter is determined off-axis and the aorta usually has a circular cross-section, the above determined incidence angle can be used to convert the determined diameter into the true diameter, when the angle of incidence is known.

It should be appreciated that a very precise measurement can be performed even when the beams are not substantially coaxial with the aorta. Typically, aligning a Doppler ultrasonic flowmeter to the aorta is difficult and not comfortable for the patient being examined. Using a device constructed in accordance with this embodiment of the present invention is generally more comfortable for the patient, since alignment is not required, and only a line of sight between the device and the aorta is necessary.

A preferred embodiment of the invention provides an ultrasonic flowmeter which further comprises signal processors and/or sensors, preferably ultrasonic, operative to estimate an angle of incidence $\alpha$ and/or an angle of reflectance $\beta$ of an ultrasonic beam on a blood vessel. Alternatively or additionally, the flowmeter comprises apparatus for determining the attenuation of ultrasonic beams in the tissue between the flowmeter and the vessel.

In a still further preferred embodiment of the invention, the ultrasonic flowmeter comprises sensors which measure the movement of the vessel wall and/or the distance of the vessel from the flowmeter.

In a preferred embodiment of the invention, separate ultrasonic transducers are used for transmitting and receiving ultrasonic beams.

In a further preferred embodiment of the invention, the instantaneous blood pressure in the vessel is determined from a measurement of the blood vessel wall movement and the flow velocity in the vessel. The blood pressure may be determined using Poiseuille's equation or electromagnetic transmission-line equations. A local impedance value of the blood vessel can be determined from general haemodynamic parameters, by measuring the complex value of the reflectance from capillaries at the end of the blood vessel or by determining the effect of the dilation of the capillaries (by exercise) on the reflectance.

In another preferred embodiment of the invention, a measured Doppler spectrum is filtered in a frequency-dependent manner to reduce artifacts. Preferably, the lower Doppler frequencies are emphasized substantially less than the higher frequencies. This filtration tends to equalize the amplitude of the Doppler spectrum, so that the amplitude of the signal is independent of the flow velocity. Since, most of the artifacts in a typical blood Doppler spectrum are usually found at the lower Doppler frequencies, emphasizing the higher frequencies as compared to the lower frequencies tends to reduce the effect of these artifacts and reduce the amplitude range of the Doppler spectrum. Detection of gas bubbles is especially enhanced by this processing technique, because gas bubbles produce a change in signal amplitude which is easier to detect on the background of a constant amplitude Doppler spectrum.

It should be appreciated that the apparatus and methods described herein apply to many types of flow with suspended particles, one example of which is blood, another is crude oil.

There is therefore provided in accordance with a preferred embodiment of the invention a method of determining the velocity of a flowing material, suspended in a liquid and flowing in a conduit, including:

irradiating the conduit with ultrasonic waves; detecting first Doppler-shifted reflections of the waves from the material, which first reflections have a positive Doppler-shift; detecting second Doppler shifted reflections of the waves from the material, which second reflections have a negative Doppler-shift; and estimating the flow velocity based on the extent of the positive and negative Doppler-shifts.

Preferably, estimating the flow velocity includes summing the first and second reflections to form a composite signal; and determining the range of Doppler-shifts in the composite signal.

Alternatively, estimating the flow velocity includes summing the spectrum of the first reflections and the spectrum of the second reflections to form a composite spectrum; and estimating the velocity from the composite spectrum.

Further alternatively, estimating the flow velocity includes calculating a first velocity based only on the first reflections; calculating a second velocity based only on the second reflections; and estimating the velocity of the flow from the first and second velocities.

Further preferably, estimating the flow velocity includes determining a maximum velocity of the flow; and determining a flow-average velocity of the flow based on the determined maximum velocity.

In a preferred embodiment of the invention estimating the flow velocity includes determining a quadric-average velocity of the flow; and determining a flow-average velocity of the flow based on the determined quadric-average velocity.

In a further preferred embodiment of the invention estimating the flow velocity includes determining the travel time of the first reflections from the material to a first detector; determining the travel time of the second reflections from the material to a second detector; and determining a first angle between the first reflections and the flow direction of the material based on the determined travel times.

Alternatively, estimating the flow velocity includes determining relative attenuation between the first reflections and the second reflections; determining the travel time of the first reflections from the material to a first detector; determining the travel time of the second reflections from the material to a second detector; and determining an attenuation per unit length of the reflections based on the determined travel times and the determined relative attenuation. More preferably, the method includes determining a first angle between the first reflections and the flow direction of the material based on the determined travel times.

A method, as described above, where the flow has a substantially circular cross-section preferably includes determining a diameter of the flowing material or of the conduit; and correcting the diameter using the first angle.

Preferably, the method includes converting the travel times to distances based on a measured velocity of ultrasound waves in soft tissue surrounding the flowing material.

In a preferred embodiment of the invention, irradiating the conduit includes:

(a) irradiating the conduit with first ultrasonic waves from a first direction such that the first waves have a component of propagation in the flow direction of the material; and (b) irradiating the conduit with second waves from a second direction such that the second waves have a component of propagation opposite the flow direction of the material, where at least a portion of first waves are reflected as the second reflections and at least a portion of the second waves are reflected as the first reflections. Preferably, the first waves and the second waves intersect. More preferably, they intersect at the conduit. Alternatively, the waves do not intersect.

In a further preferred embodiment of the invention, the method includes detecting third Doppler-shifted reflections of the ultrasonic waves from the material, and estimating the flow velocity includes estimating the velocity based on the first, second and third reflections. Preferably, the first second and third reflections are not co-planar.

In some embodiments of the invention irradiating the conduit includes irradiating the conduit with ultrasonic waves at a single direction.

In embodiments of the invention which include detecting three reflected waves, irradiating the conduit preferably includes irradiating the conduit from first, second and third locations and detecting first, second and third reflections preferably includes:

(a) detecting first reflections of waves from the first location;

(b) detecting second reflections of waves from the second location; and (c) detecting third reflections of waves from the third location.

In a preferred embodiment of the invention, estimating the velocity of the flow includes estimating the velocity without individually correcting velocity estimates derived from the first and second reflections for deviations related to the first angle.

Another embodiment of the invention provides for a method of determining the pressure exerted by the flowing material on the conduit, including determining the velocity of the flow as described above, determining the cross-section of the conduit; determining an equivalent length of the conduit and determining the pressure from the determined cross-section of the conduit, the determined equivalent length and from the determined velocity. Preferably, where the flow is pulsile, determining the equivalent length includes determining a velocity of the pulse wave; determining a travel time of a pulse wave along the conduit; and determining the equivalent length from the determined pulse wave velocity and the determined travel time.

There is provided in accordance with another preferred embodiment of the invention a method of determining a first angle between first Doppler-shifted reflections of ultrasonic waves from a flowing material, suspended in a liquid and flowing in a conduit, and the flow direction of the material, including determining a first estimate of the velocity of the flow from the first reflections determining a second estimate of the velocity of the flow from second reflections of the waves from the material; and calculating the incidence angle based on the velocity estimates and a known angle between the first and second reflections.

Preferably, when the flow has a substantially circular cross-section the method further includes determining a diameter of the flowing material or of the conduit; and correcting the diameter using the first angle.

When the flow is pulsile, a method according to the above described embodiments of the invention preferably includes determining a particular phase of the pulse of the flow of the first reflections; determining a time delay such that the second reflections have the particular phase; and delaying a signal generated by one of the first and second reflections based on the time delay. Preferably, the particular phase is determined from changes in the diameter of the conduit. More preferably, the changes in diameter are determined using ultrasonic sensors. Optionally, the changes in diameter are determined from reflections from the conduit.

Additionally or alternatively, the particular phase is determined from the first Doppler-shifted reflections from the material.

In the above described preferred methods, the reflections are preferably from substantially a same portion of the material. Alternatively, the reflections are from substantially different portions of the material.

There is further provided in accordance with a preferred embodiment of the invention a method of determining the velocity of a flowing material, suspended in a liquid and confined by a conduit, including irradiating the conduit with ultrasonic waves from a radiator location; determining a first distance between a first transducer, having a known positional relationship to the radiator location, and the flowing material; determining a second distance between a second transducer, having a known positional relationship to the radiator location, and the flowing material; determining an incidence angle between the direction of propagation of the ultrasonic waves and the flowing material based on the determined distances and the positional relationships; estimating an uncorrected velocity of the flow from Doppler-shifted reflections of ultrasound waves; and correcting the uncorrected velocity based on the determined incidence angle.

Preferably, the above described preferred embodiments of the invention include filtering at least one of the reflections so that signals having higher Doppler-shifts are emphasized more than those having lower Doppler shifts. Preferably, filtering includes filtering at least one of the reflections to have a substantially velocity independent peak signal-amplitude.

In a further preferred embodiment of the invention, the orientation of an ultrasonic receiver is changed to detect at least one of the reflections. Preferably, changing the orientation includes changing a lobe direction of an ultrasonic scanner. Alternatively or additionally, changing the orientation includes changing the orientation if Doppler-shifted reflections are not detected.

There is further provided, in accordance with a preferred embodiment of the invention, a method of non-invasivly determining local blood pressure at a location in a circulatory system bounded at one end by a heart and at the other end by capillaries, including determining a local impedance to the flow of blood; determining an end impedance to the flow of blood at the capillary end of the system; determining the blood flow volume based on a flow velocity determined according to any of the above methods; and determining the instantaneous local blood pressure at the location from the local impedance, the end impedance and the flow volume.

Preferably the impedances are determined by determining a reflectance at the capillary end; and determining the impedances from the reflectance. Further preferably, the method includes determining the complex value of the reflectance by measuring the amplitude and phase of reflected pulse waves.

Preferably, determining a reflectance includes determining a reflectance before dilating the capillaries; and determining a second reflectance after dilating the capillaries.

There is further provided in accordance with another preferred embodiment of the invention, a method of detecting gas bubbles suspended in a flowing liquid, having suspended material therein and confined by a conduit, including irradiating the conduit with ultrasonic waves; detecting. Doppler-shifted reflections from the material; filtering the reflections in a frequency-dependent manner to have a substantially velocity-invariant maximum signal amplitude, and detecting gas bubbles when the amplitude of the filtered reflections is above a given limit.

There is also provided, in accordance with a preferred embodiment of the invention, a method of mapping of a blood pressure in a body including:

non-invasivly determining a time-dependent blood pressure at a first location on the body; and repeating the blood pressure determination at a plurality of locations.

There is further provided, in accordance with yet another preferred embodiment of the invention, a method of determining the presence of a stenosis between a first location and a second location, including non-invasivly determining a first local blood pressure at the first location; non-invasivly determining a second local blood pressure at the second location; and comparing the first and second local blood pressures.

Preferably, the invention is practiced in the human body, where the conduit is a blood vessel.

There is further provided, in accordance with a preferred embodiment of the invention, an ultrasonic flowmeter for determining the velocity of a material, suspended in a liquid and flowing in a conduit, including:

a first ultrasonic transducer which transmits first ultrasonic waves towards the conduit at a first angle to the direction of the flow of the material and which receives first Doppler-shifted reflections of the first waves from the material;

a second ultrasonic transducer, spaced from the first transducer, which transmits second ultrasonic waves, at a second angle to the first waves, towards the conduit and which receives second Doppler-shifted reflections of the second waves from the material; and a controller which estimates the first angle based on the distance between the first and second transducers, the second angle and the first and second reflections and which determines the velocity of the flow based on the determined first angle and the first reflections, where the propagation directions of the first and second waves have components in the same direction relative to the flow direction of the material.

Preferably, the flowmeter includes a third ultrasonic transducer, spaced from the first and second transducers, which transmits third ultrasonic waves towards the conduit, at a third angle to the first waves and at fourth angle to the second waves and which receives third Doppler-shifted reflections of the third waves from the material, and where the controller estimates the first angle based on the distances between the transducers, the second, third and fourth angles and the first and third reflections.

Preferably, the waves are a pulsed sequence of waves and the controller determines the timing of pulses which are Doppler-shifted by the material to determine an off-axis-extent of the conduit.

Further preferably, the controller calculates a diameter of the conduit based on the determined oblique diameter and the determined first angle and the controller estimates the flow volume in the conduit based on the determined conduit diameter and the determined velocity.

Preferably, where the flow is pulsile, the controller analyzes the first, second and third Doppler-shifted reflections to determine a time delay between the three reflections is based on the pulse velocity of the flow.

There is further provided, in accordance with a preferred embodiment of the invention, an ultrasonic flowmeter for determining the velocity of a material, suspended in a liquid and flowing in a conduit, including:

a first ultrasonic transducer which transmits first ultrasonic waves towards the conduit at a first angle to the direction of the flow of the material and which receives first Doppler-shifted reflections from the material;

a second ultrasonic transducer, spaced from the first transducer, which transmits second ultrasonic waves, at a second angle to the first waves, towards the conduit and which receives second Doppler-shifted reflections from the material; and a controller which determines the velocity of the flow by summing the first and second reflections, where the propagation directions of the first and second waves have components which are parallel to the direction of the flow of the material and opposite from each other. Preferably, the controller estimates velocity without individually correcting velocity estimates derived from the first and second reflections for deviations related to the first angle.

There is also provided, in accordance with a preferred embodiment of the invention, an ultrasonic flowmeter for determining the velocity of a material, suspended in a liquid and flowing in a conduit, including a first ultrasonic transducer which transmits first ultrasonic waves towards the conduit; a second ultrasonic transducer spaced from the first transducer which receives first Doppler-shifted reflections of the first waves from the material; a third ultrasonic transducer spaced from the second transducer which receives second Doppler-shifted reflections of the first waves from tine material; and a controller which determines the velocity of the flow by summing the first and second reflections.

There is further provided, in accordance with a preferred embodiment of the invention, an ultrasonic flowmeter for determining the velocity of a material, suspended in a liquid and flowing in a conduit, including three ultrasonic transducers, having non-co-planar reception lobes which intersect at the flowing material and which receive first, second and third Doppler-shifted reflections from the material; and a controller which determines the velocity of the flow by combining the first, second and third reflections. Preferably, the flowmeter includes a transmitter having a transmission lobe which intersects the reception lobes of each of the three transducers and which transmits ultrasonic waves to the conduit.

There is further provided, in accordance with still another preferred embodiment of the invention, an ultrasonic flowmeter for determining the velocity of a material, suspended in a liquid and flowing in a conduit, including a first transducer which transmits first ultrasonic waves to the conduit; a second transducer which receives first Doppler-shifted reflections of the first waves from the material, which first reflections have a positive Doppler-shift; a third transducer which transmits second ultrasonic waves, to the conduit; a fourth transducer which receives second Doppler-shifted reflections of the second waves from the material, which second reflections have a negative Doppler-shift; and a controller which estimates the flow velocity based on the extent of the positive and negative Doppler-shifts. Preferably, the controller sums the first and second reflections to form a composite signal and determines the range of Doppler-shifts in the composite signal.

Alternatively, the controller sums the spectrum of the first reflections and the spectrum of the second reflections to form a composite spectrum and estimates the velocity from the composite spectrum.

Alternatively, the controller calculates a first velocity based only on the first reflections. calculates a second velocity based only on the second reflections and estimates the velocity of the flow from the first and second velocities.

In a further preferred embodiment of the invention, where the flow is pulsile, the conduit has a variable extent and where either the first or the second transducers receives first diameter-change indicating reflections from the conduit and either the third or the fourth transducers receive second diameter-change indicating reflections from the conduit, the controller determines a delay in the propagation of a particular pulse phase between the first and second diameter-change indicating reflections and delays a signal generated by the first Doppler-shifted reflections relative to a signal generated by the second Doppler-shifted reflections based on the determined delay.

In a preferred embodiment of the invention, where the flow is pulsile, the conduit has a variable extent and where the first waves intersect the conduit at a first location and the second waves intersect the conduit at a second location, the flowmeter includes:

a first diameter-change detecting ultrasonic transducer which transmits third ultrasonic waves to the conduit and which receives first diameter-change indicating reflections of the third waves; and a second diameter-change detecting ultrasonic transducer which transmits fourth ultrasonic waves to the conduit and which receives second diameter-change indicating reflections of the fourth waves, where the controller determines a delay in the propagation of a particular pulse phase between the first and second locations from the diameter-change indicating reflections and delays a signal generated by the first Doppler-shifted reflections relative to a signal generated by the second Doppler-shifted reflections based on the determined delay.

Preferably, the diameter-change indicating reflections include reflections from the material. Alternatively, the diameter-change indicating reflections include reflections from the conduit. Alternatively or additionally, the first diameter-change detecting ultrasonic transducer includes a transmitter and a receiver and the first diameter-change detecting ultrasonic transducer includes a transmitter and a receiver.

In a preferred embodiment of the invention, the flowmeter includes an imaging sensor which determines when the flowmeter transmits waves impinging the conduit.

Preferably, in a flowmeter as described above, the transducers include phased-array scanners having electronically controlled ultrasonic orientations and the controller directs the orientations of the transducers towards the flow. Preferably, the controller directs the orientations of the transducers with respect to each other.

Alternatively or additionally, the transducers have mechanically controlled ultrasonic orientations which enable coordinated orientation changes of the transducers.

In a preferred embodiment of the invention, the controller filters at least one of the reflections in a frequency-dependent manner so that it has a substantially velocity-invariant maximum signal amplitude.

There is further provided, in accordance with a preferred embodiment of the invention, a gas bubble detector for detecting gas bubbles in a flow of a material suspended in a liquid, including an ultrasonic flowmeter which generates a Doppler-shifted signal of at least one wave transmitted to the flowing material; a filter which filters the signal so that high frequencies are emphasized over low frequencies; and an amplitude detector which generates an alarm when the amplitude of the filtered signal is greater than a given value. Preferably, the filter filters the signal to have a velocity-invariant maximum signal amplitude. Such a gas detector is preferably included in a cardio-pulmonary bypass device, which includes:

a first tube which conveys blood from a patient to an aerator; a second tube which conveys blood from the aerator to the patient; and a gas bubble detector, which detects gas bubbles in the blood in at least one of the first and second tubes.

There is further provided, in accordance with a preferred embodiment of the invention, an ultrasonic flowmeter for determining the velocity of a material, suspended in a liquid and flowing in a conduit, including a least one transducer which transmits ultrasonic waves to the conduit and which receives Doppler-shifted reflections from the material; and a controller which estimates the velocity based on the reflections to within 5% of the velocity, where the velocity estimate does not include corrections for deviations caused by up to 15° uncertainty related to an angle between the transmitted waves and the conduit.

There is further provided, in accordance with a preferred embodiment of the invention, an ultrasonic flowmeter for determining the velocity of a material, suspended in a liquid and flowing in a conduit, including a least one transducer which transmits ultrasonic waves to the conduit, at a first angle between the waves and the conduit, of between 10°–170° and having an uncertainty, and which receives Doppler-shifted reflections from the material; and a controller which estimates the velocity based on the reflections to within an error, compared to the velocity, of less than the cosine of the uncertainty, where the estimation of the velocity does not include corrections for deviations caused by the uncertainty.

There is further provided, in accordance with a preferred embodiment of the invention, a method of determining the velocity of a flowing material, suspended in a liquid and flowing in a conduit, including transmitting ultrasonic waves to the conduit; receiving Doppler-shifted reflections from the material; and estimating the velocity based on the reflections to within 5% of the velocity, without correcting for deviations caused by up to 15° uncertainty related to an angle between the transmitted waves and the conduit.

There is further provided, in accordance with a preferred embodiment of the invention, a method of determining the velocity of a flowing material, suspended in a liquid and flowing in a conduit, including:

transmitting ultrasonic waves to the conduit at a first angle between the waves and the conduit, of between 10°–70° and having an uncertainty; receiving Doppler-shifted reflections from the material; and estimating the velocity based on the reflections to within an error, compared to the velocity, of less than the cosine of the uncertainty, without correcting for deviations caused by the uncertainty.

There is further provided in accordance with a preferred embodiment of the invnetion a as bubble detector for detecting gas bubbles in a flow of a material suspended in a liquid. including, an ultrasonic flowmeter which generates a Doppler-shifted signal of at least one wave transmitted to the flowing material; and an amplitude detector which generates an indication signal when the amplitude of the filtered signal is greater than a frequency dependent value, which value is higher for low frequencies than for high frequencies.

BRIEF DESCRIPTION OF THE DRAWINGS

The present invention will be more fully understood from the following detailed description of the preferred embodiments thereof, taken together with the drawings in which:

FIGS. 10A–D show the effect of a stenosis on haemodynamic properties of flow in a blood vessel;

FIG. 14A is a schematic block diagram of an ultrasonic generator useful for preferred embodiments of the invention;

FIGS. 14B and 14C are graphs showing waves generated by the generator of FIG. 14A;

DETAILED DESCRIPTION OF THE PREFERRED EMBODIMENTS

Figure 1A:
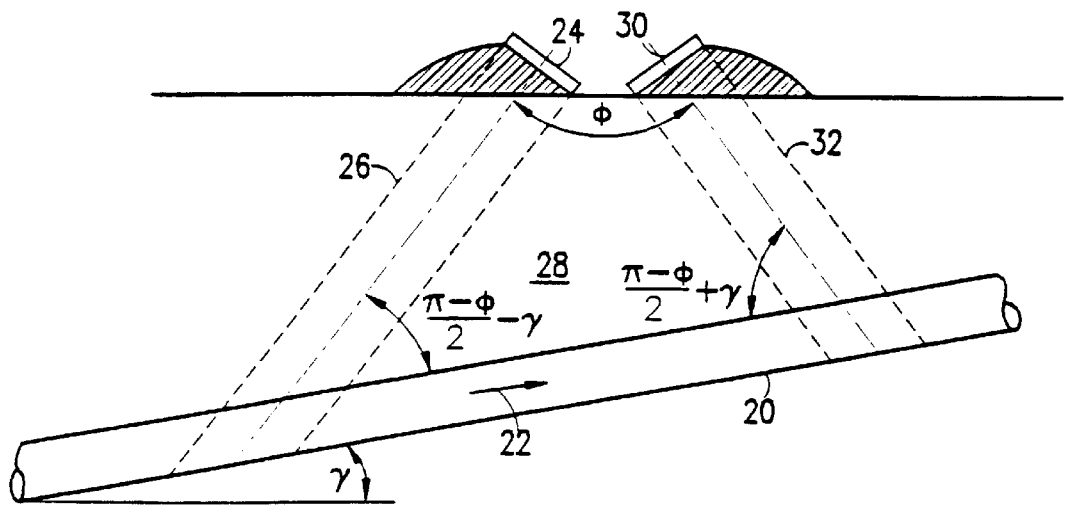
FIG. 1A is a schematic side view of a method of determining flow velocity according to a preferred embodiment of the invention.
Figure 1B:
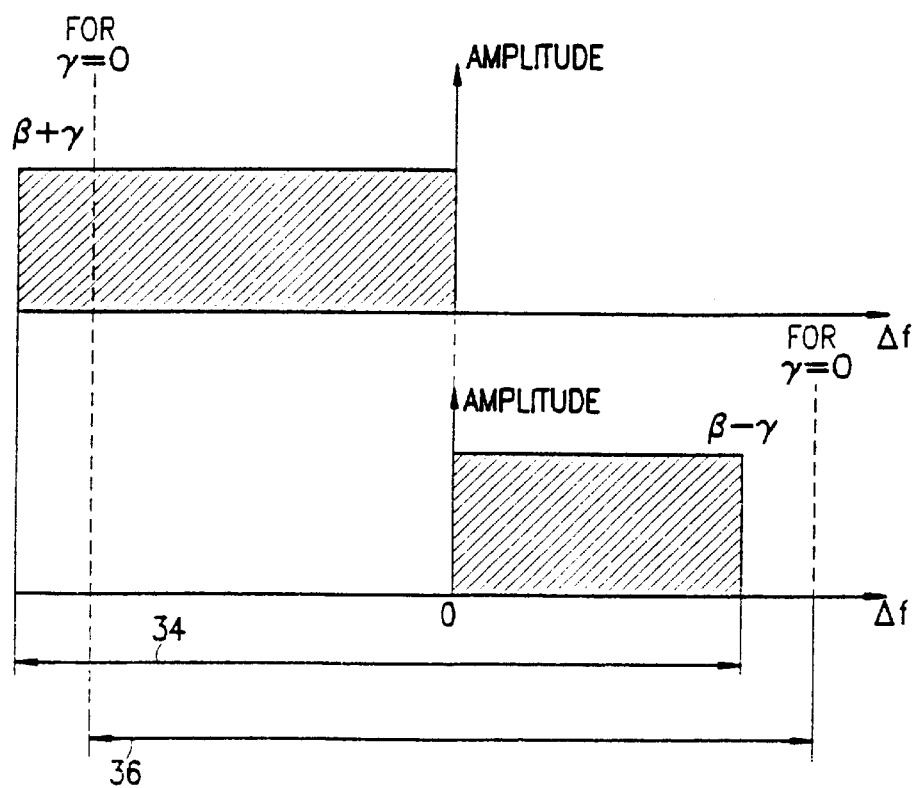
FIG. 1B is a graph showing an effect of a small angular deviation on signal received in the method of FIG. 1A.

FIG. 1A is a schematic side view illuminating flow velocity determination according to a preferred embodiment of the invention. A blood vessel 20 has a blood flow 22 generally along the long axis of vessel 20. A first ultrasonic transducer 24 transmits a first pencil beam 26 through intervening soft-tissue 28 and to blood flow 22 at a first position on vessel 20, so that a first Doppler-shifted reflection from flow 22 is detected by transducer 24. A second ultrasonic transducer 30 transmits a second pencil beam 32 to blood flow 22 at a second position on vessel 20, so that a second Doppler-shifted reflection from flow 22 is detected by transducer 30. FIG. 1B is a graph which shows the relationship between the spectrum of the first Doppler-shifted reflection and the spectrum of the second Doppler-shifted reflection. The X-axis origin is at the transmitted frequency Pencil beam 26 is transmitted generally opposite the direction of flow 22, therefore, the Doppler-shift of the reflectance signal is positive, while pencil beam 32 is transmitted generally in the direction of flow 22, so that the Doppler-shift of the reflectance signal is negative. Reference number 34 indicates the total extent of the Doppler shift, from the highest frequency in the Doppler-shifted spectrum of pencil beam 26 to the lowest frequency in the Doppler-shifted spectrum of pencil beam 32. According to equation (1), extent 34 is equal to $$\delta = \frac{2v}{\lambda}\cos\left(\frac{\pi-\phi}{2}+\gamma\right) - \frac{2v}{\lambda}\cos\left(\frac{\pi-\phi}{2}-\gamma\right) = \frac{4v}{\lambda}\cos\left(\frac{\pi-\phi}{2}\right)\cos(\gamma) \quad (2)$$

Where $\gamma$ is the angle between vessel 20 and the surface of soft tissue 28 and $\phi$ is the angle between beams 26 and 32. In the special case where $\gamma=0$ the extent is $$\delta = \frac{4v}{\lambda}\cos\left(\frac{\pi-\phi}{2}\right) \quad (3)$$

which is indicated by reference 36 of FIG. 1B.

It should be appreciated that, unlike equation (1), neither equation (2) nor equation (3) depend on the angle of incidence. Rather they depend on a known angle between the pencil beams. $\gamma$ is typically near zero, so the error resulting from using equation (3) instead of equation (2) is very small, as shown below.

As can be appreciated, the velocity of flow 22 can be determined from the combined Doppler spectrum using any of the methods well known in the art. For example, it may be advantageous to average several acquired spectra to reduce noise. Alternatively or additionally, results of processing as described herein may be averaged or otherwise processed to reduce error-rates.

Figure 1C:
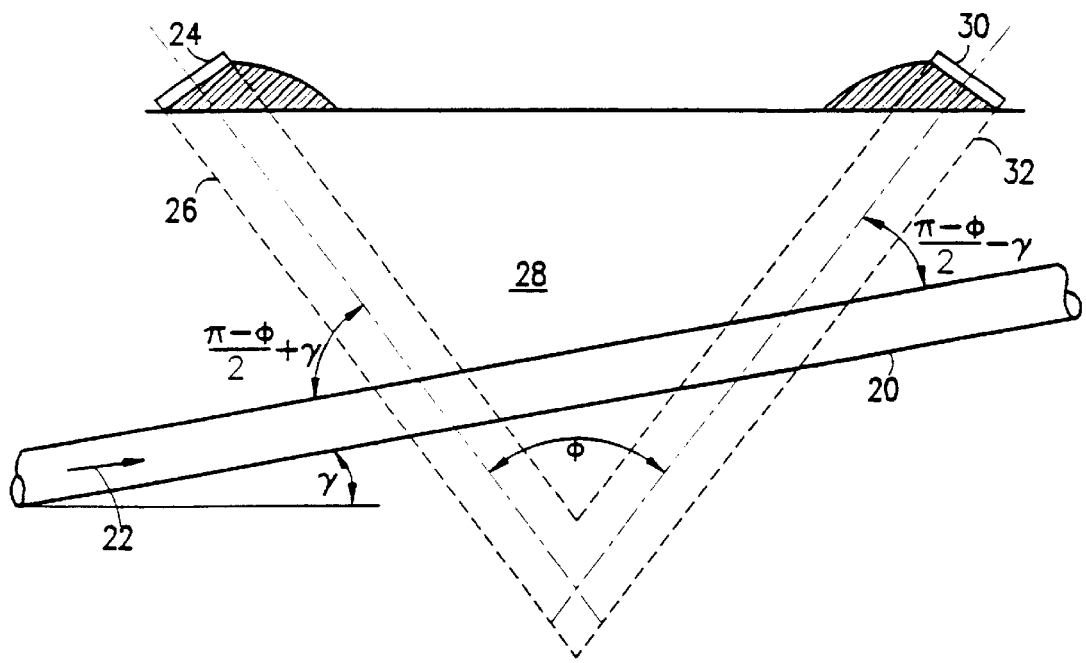
FIG. 1C is a schematic side view of a method of determining flow velocity according to another preferred embodiment of the invention.

FIG. 1C shows an alternative embodiment of the invention, where pencil beams 26 and 32 intersect with vessel 20 at neighboring locations, so that substantially the same portion of flow 22 is measured.

It should be appreciated that when pencil beams 26 and 32 do not intersect each other on vessel 20, such as shown in FIGS. 1A and 1C, the pulse wave velocity in the blood vessel should be taken into account. Thus, acquisition of Doppler reflection signals is synchronized to the pulse phase. For example, if beam 26 intersects vessel 20 at a point one cm from the intersection point of beam 32 with vessel 20 and the pulse velocity is 300 cm/sec, a time delay of 0.0033 seconds is required between the signals from transducer 24 and transducer 30 so that their Doppler spectra can be matched. Preferably, the pulse wave is measured using an ultrasonic sensor, as described below with reference to FIGS. 6A and B.

Figure 2:
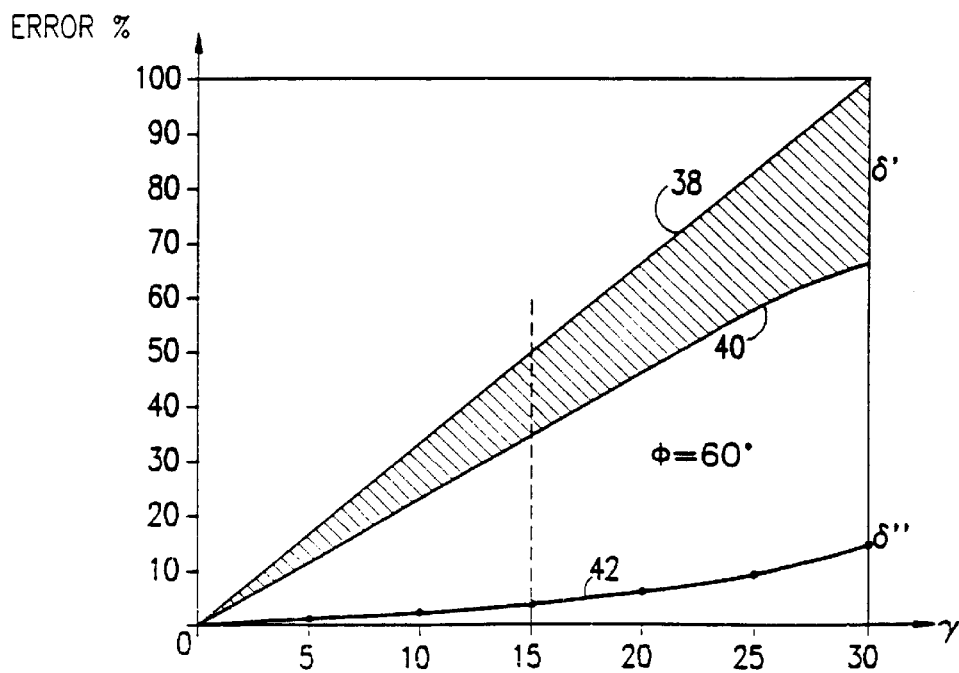
FIG. 2 is a graph comparing an expected error using a flowmeter according to a preferred embodiment of the present invention to an expected error when using a standard Doppler flowmeter.

FIG. 2 is a graph which shows an expected error of velocity estimation using either one of the above described embodiments and equation (3), if the unknown angle γ is assumed to be zero. The angle between the beams φ is 60°, which is equivalent to an angle of incidence of 30°. The X-axis is the error in the estimation of the incidence angle and the Y-axis is the velocity error as a percentage of the true velocity. A curve 42 shows the error which should be expected when equation (3) is used to determine the velocity of flow 22, instead of equation (2). A curve 38 (and a curve 40) show the maximum (and minimum) expected error where the velocity is determined using a standard Doppler flowmeter. It should be appreciated that at 15 degrees, which is a maximum typical angle between blood vessels and the skin surface, the error, as shown by curve 42, is under 5% while the error, as shown by curves 38 and 40, is over 30%.

The inventor has determined that many error-causing artifacts are found in the lower Doppler-shifted frequencies rather than the higher ones. In addition, the signal amplitude of a low velocity flow is larger than at the signal amplitude of a high velocity flow, which may result in non-optimal amplification when using limited bandwidth amplifiers. In a preferred embodiment of the invention, the Doppler spectrum is filtered in a frequency dependent manner, so that frequencies with a high Doppler-shift are emphasized more than frequencies with a low Doppler-shift. As a result, the maximum amplitude of the Doppler-shifted spectrum is substantially unaffected by the flow velocity. Preferably, the frequency-dependent filtration is performed on the output signal of the ultrasonic transducers using an analog filter. Alternatively or additionally, the output signal is first digitized.

Figure 3A:
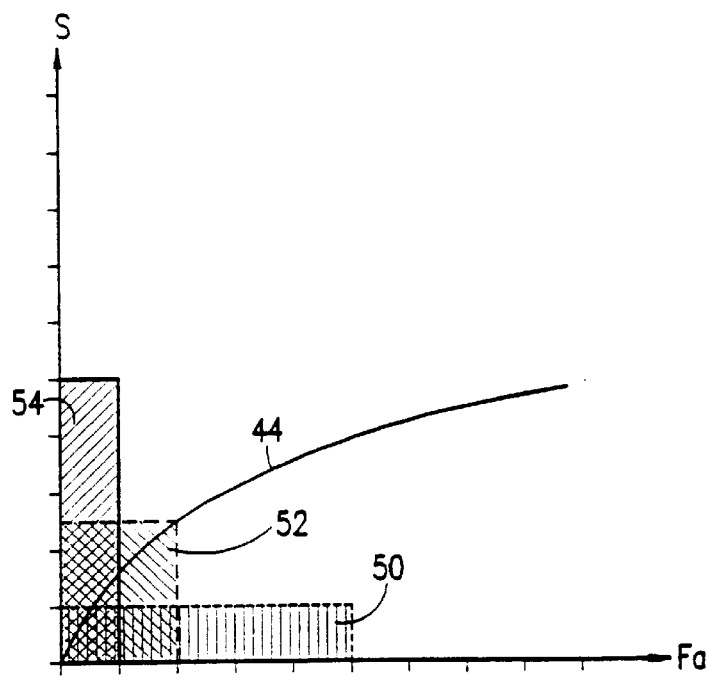
FIG. 3A is a graph which shows the spectra of a plurality of Doppler signals.
Figure 3B:
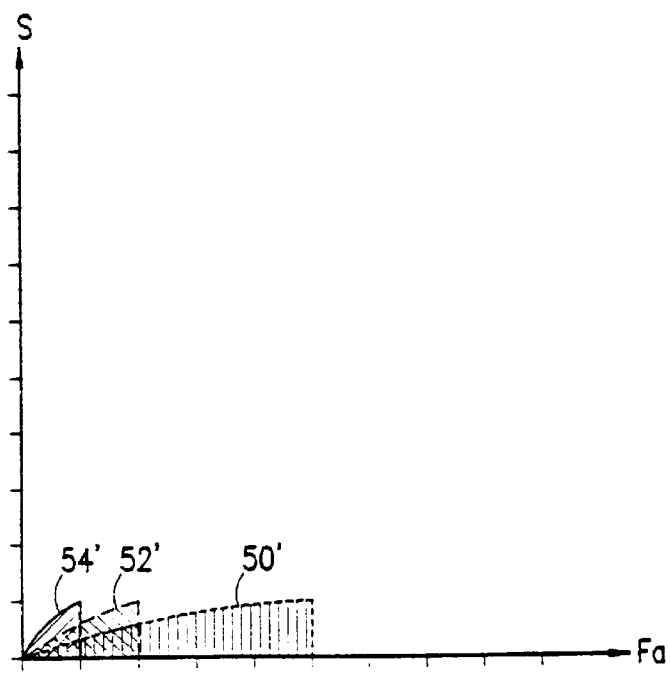
FIG. 3B is a graph which shows the signals of FIG. 3A after filtration in a frequency dependent manner in accordance with a preferred embodiment of the invention.

FIG. 3A shows a plurality of unfiltered Doppler-shifted spectra 50, 52 and 54. It should be noted that the integrals of the three spectra 50, 52 and 54 are substantially equal. FIG. 3B shows filtered spectra 50', 52' and 54' which correspond to spectra 50, 52 and 54, corrected in accordance with a function 44. The filtered spectra all have substantially the same maximum amplitude. Other beneficiary effects of filtering using function 44 will be described in greater detail below.

Figure 4:
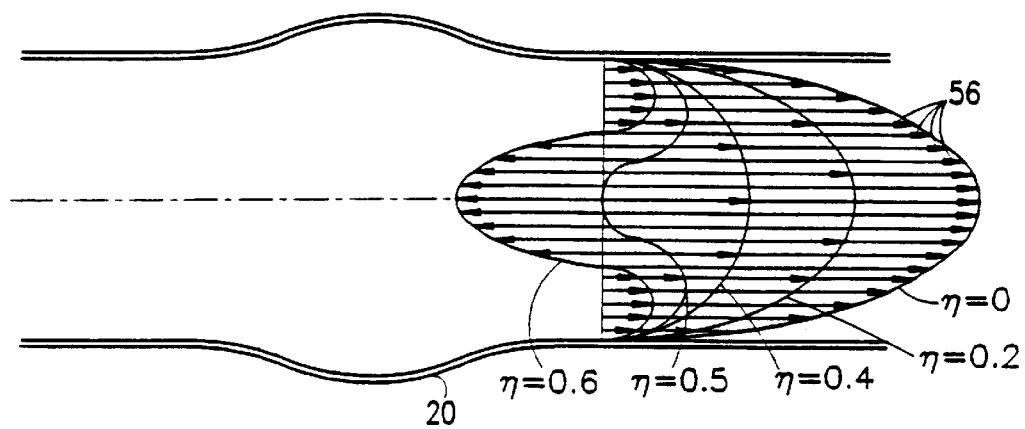
FIG. 4 is a cross-section through a blood vessel showing laminar and pulsile flow.

FIG. 4 is a cross-sectional view of blood vessel 20 showing the blood flow velocity distribution in laminar and pulsile flow conditions. The magnitude of a plurality of arrows 56 indicates the flow velocity at a certain distance from the vessel wall. η is a reflection coefficient which indicates the amount of pulsatility in arterial blood flow. Typically, at the peak of the pulse wave all of the blood in vessel 20 flows in one direction. However, when the peak of the pulse wave passes, a reflected wave from the end of vessel 20 urges the blood in the opposite direction. At η=0, the flow is entirely laminar; at η=0.5 some of the flow is on the verge of flowing back; and at η=0.6 part of the blood is actually flowing back. In most arteries, η<0.5 during most of the cardiac cycle. The inventor has found that in cases where η<0.5 the blood velocity is correctly determined using the methods as described herein.

Since the blood velocity is not the same over the entire cross-section of blood vessel 20, several different velocities can be used to represent the flow velocity. One such velocity is the maximum velocity in vessel 20. The maximum velocity can be determined from the maximum Doppler shift caused by the blood flow. Another representative velocity is the flow-average velocity, which when multiplied by the cross-sectional area of the vessel, yields the blood volume flow rate. The flow-average velocity can be determined from the Doppler spectrum by treating the Doppler spectrum as a histogram and determining the velocity represented by the median frequency shift. A third representative velocity is the quadric average-velocity, in which each velocity is given a weight equal to the velocity squared.

Figure 5:
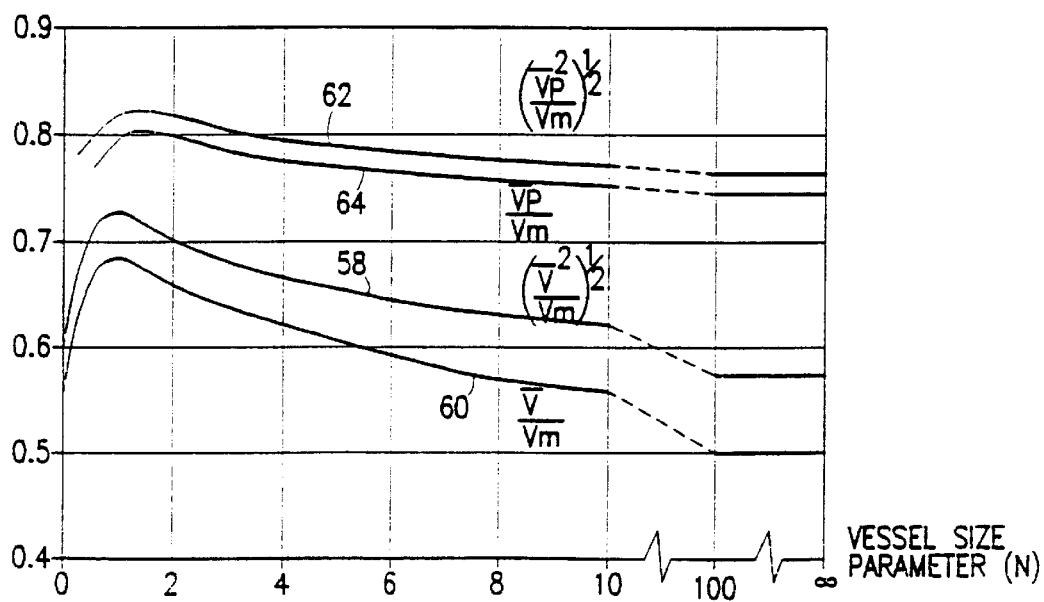
FIG. 5 is a graph which shows the constancy of ratios between velocities which are determined in accordance with a preferred embodiment of the invention.

Interestingly, the ratio between the different velocities is substantially constant under varying conditions. In particular, the ratios are constant even when the flow is relatively pulsile η=0.5. FIG. 5 is a graph which shows the dependence of several velocity ratios on the diameter of blood vessel 20. In small blood vessels, the distribution of red-blood cells is not constant in the vessel, rather, red blood cells tend to concentrate in the center of the vessel. Since red blood cells are the main reflector of ultrasonic waves in the blood, a change in their distribution can affect the Doppler spectrum, and as a result, the ratios between the velocities. A curve 60 represents the ratio between the flow-average speed and the maximum speed. The X-axis is a parameter which represents the size of the blood-vessel, where medium sized arteries have an n-value which is greater than 100. As shown in FIG. 5, in medium and larger blood vessels the ratio between the flow-average velocity and the maximum velocity is asymptotic to 0.5. A curve 58 represents the ratio between the quadric-average velocity and the maximum velocity, which is asymptotic to 0.577.

As described above, in a preferred embodiment of the invention, the Doppler spectrum is filtered in a frequency-dependent manner. The inventor has found that the main effect of frequency-dependent filtration on the velocity ratios is to change their asymptotic values. Thus, a curve 64 represents the ratio between the flow-average velocity determined from a signal filtered in a frequency-dependent manner and the maximum velocity, where the ratio is asymptotic to 0.75. A curve 62 represents the ratio between the quadric-average velocity of a signal filtered in a frequency-dependent manner and the maximum velocity, where the ratio is asymptotic to 0.775. A further benefit of the frequency-dependent filtration is that the velocity ratios remain constant even in cases when η=0.6. In addition, if the type of flow is known, for example, if flow is laminar, the distribution of flow velocities in vessel 20 can be reconstructed from the maximum velocity (which is unaffected by the filtering).

One aspect of the present invention relates to non-invasive determination of the instantaneous blood pressure. Blood vessels are composed of an elastic material, so that when the local blood pressure chances, the blood vessel changes its diameter in response to the pressure change. It is known in the art that a blood pressure graph and a vessel diameter graph are generally equivalent, except for scale. Thus, if the changes in vessel diameter are monitored, the blood pressure can be determined therefrom in combination with several other haemodynamic parameters, as described below.

Figure 6A:
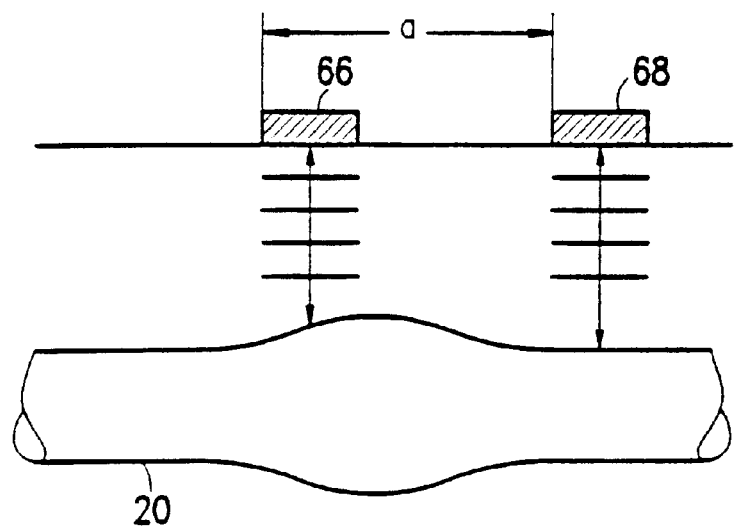
FIG. 6A is a schematic side view of apparatus for determining a pulse wave velocity and changes in the diameter of the blood vessel, according to a preferred embodiment of the invention.
Figure 6B:
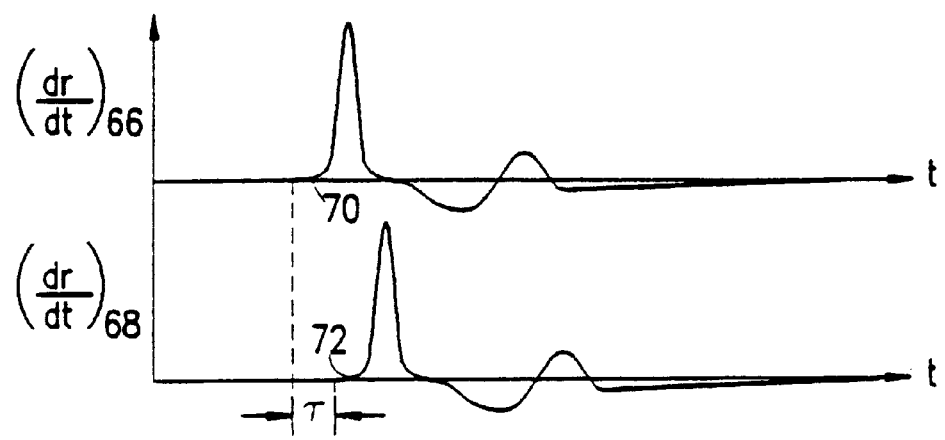
FIG. 6B is a graph showing diameter chancre rates as determined by the apparatus of FIG. 6A.

FIG. 6A shows a preferred method of determining changes in a diameter of blood vessel 20. An ultrasonic transducer 66 is oriented perpendicular to blood vessel 20 and continuously measures the distance to blood vessel 20 using methods well known in the art, such as echo-time. When vessel 20 dilates due to increased blood pressure, the travel time of an ultrasonic wave from transducer 66 to vessel 20 and back is reduced by an amount corresponding to the change in the diameter of blood vessel 20. Preferably, determination of the diameter of vessel 20 is combined with a determination of the pulse wave velocity. To this end, a second transducer 68, located a known distance from transducer 66, also measures the changes in the diameter of vessel 20. FIG. 6B is a graph showing the derivatives of the signals from transducers 66 and 68, illuminating changes in the velocity of the vessel wall. The pulse wave velocity can be determined from FIG. 6B by determining the time delay between transducer 66 and transducer 68. One preferred method is by determining a cross-correlation between the two signals. Another method detects a change 70 in the diameter of the vessel after a relatively long period of no change and determines a delay until a similar change 72 is detected in the second signal. Such a change can be detected for example, by detecting the existence of a Doppler-shift in the reflections from the vessel wall. The distance between transducers 66 and 68 is known, so the pulse wave velocity can be calculated. The delay time and/or associated changes in radius can be directly utilized to correct errors in velocity estimation due to non-intersecting beams, as described above with reference to FIG. 1C.

Figure 7:
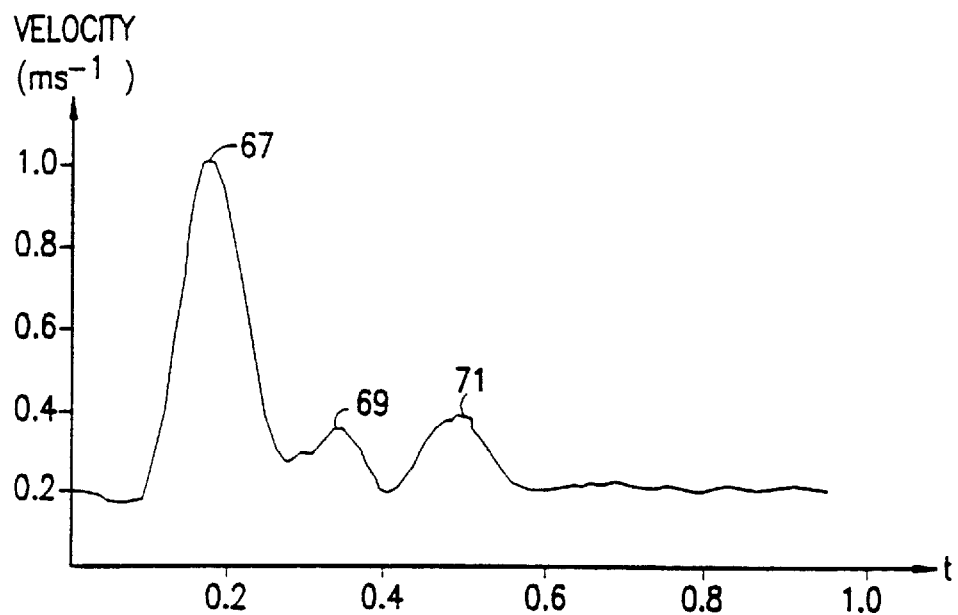
FIG. 7 is a graph showing a flow-average blood velocity as a function of time in a specific blood vessel.
Figure 8:
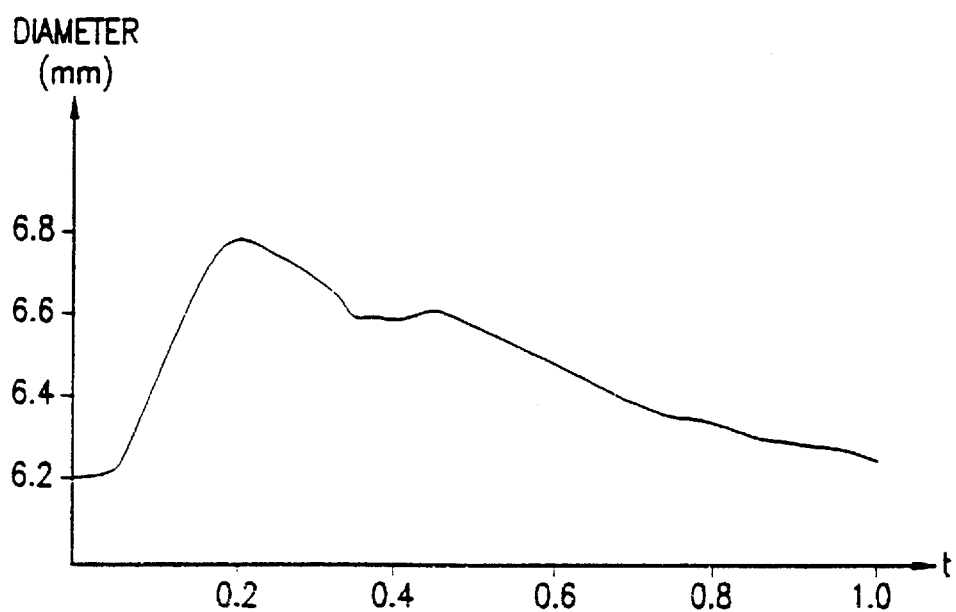
FIG. 8 is a graph showing the diameter of the blood vessel of FIG. 7 as a function of time.

FIG. 7 is a graph showing the area-average flow velocity as a function of time. A peak 67 corresponds to the main pulse wave. It should be appreciated that the pulse wave rapidly reaches the end of the circulatory system and is reflected back. Since the pulse wave velocity is typically 2–3 meters/second and the circulatory system is only ~1 meter long, the reflection from the end is usually superimposed on the pulse wave. Thus, a peak 69 is actually the result of subtracting the reflected wave from peak 67. A peak 71, which has a positive amplitude is the reflection of the reflected wave from the aortic valve in the heart. FIG. 8 is a graph showing the changes in the vessel diameter in response to the pulse wave. It should be noted that reflected waves can have either a positive or a negative amplitude, based on the phase of the reflection.

Poiseuille's equation can be used to determine the blood pressure if an imprecise estimate of pressure is sufficient. Typically, the estimated systole pressure is within 15% of the correct value and the estimated diastole pressure is significantly less precise. Poiseuille's equation, which assumes that the diameter of the blood vessel does not change, relates he blood pressure, P, to a volume velocity, V, and hydraulic impedance. Hydraulic impedance includes: the vessel radius, r, blood viscosity, $\mu$ and the length of the vessel, l:

$$P = \frac{8\mu \cdot l \cdot V}{\pi \cdot r^4} \qquad (4)$$

An equivalent length l can be determined by dividing the pulse wave velocity by half the time between the pulse and the re-reflection of the reflection of the reflected pulse from the heart.

The well known Navier-Stokes hydrodynamic equations can be used to determine the pressure if the diameter of the blood vessel is assumed to change. This is conveniently carried out using a transmission-line analogy. It is known in the art, that hydrodynamic equations are mathematically equivalent to electromagnetic transmission line equations, with voltage equivalent to pressure and current equivalent to flow. In the body, the length of the "transmission line" (blood vessel) is less than half the wavelength of the pulse wave (which is 2–3 meters), so attenuation may be ignored in a first order approximation.

The following (complex) equations apply:

$$Ptotal = Pforward + Preflected \qquad (5)$$

Ptotal, the local blood pressure, is composed of the sum of the direct pressure of the pulse wave, Pforward, and the pressure from the reflected pulse wave, Preflected.

$$R = \frac{Preflect}{Pforward} \qquad (6)$$

Where R is a reflection coefficient of the distal end of the circulatory system.

$$R = \frac{Ptotal - Zi \cdot V}{Ptotal + Zi \cdot V} \qquad (7)$$

Where Zi is the local impedance of the blood vessel.

$$Ptotal = Ze * Ve \qquad (8)$$

Where Ze is the impedance of the end of the circulatory system and Ve is the volume velocity at the end of the circulatory system (which is equal to V). Thus, $$R = \frac{Ze - Zi}{Ze + Zi} \qquad (9)$$

To solve equations (5)–(9), the impedances Ze and Zi must be known. One way to determine the impedances is tram the dynamic diameter of the blood vessel, the pulse wave velocity, reflectance R and viscosity of the blood $\mu$. Additional details regarding determining the vascular impedance may be found in the book "The Fluid Mechanics of Large Blood Vessels", Pedly T. J., Cambridge University Press, Cambridge, 1980.

Another way to determine Ze and Zi is from the reflections of the pulse wave. If the complex value of reflectance R is determined, Ze and Zi can be determined from equation (9) and the following equation:

$$\frac{Ze}{Zi} = \frac{1 - (ReR)^2 + (ImR)^2 + i \cdot 2 \cdot ImR}{(1 - ReR)^2 + (ImR)^2} \qquad (10)$$

Alternatively, a Nyquist diagram can be used to determine Ze directly from reflectance R. The phase shift and amplitude of reflectance R can be determined by measuring the phase and amplitude of at least one pulse wave reflectance. The amplitude can be determined directly from FIG. 7, such as peak 71 (which is reflected twice). The phase (time shift) can be determined from the equivalent length l and the pulse wave velocity. Zi can then be determined using equation (9). It should be noted that in some cases, for example when performing exercise, Ze is lowered, so more reflections are discernible in FIG. 7.

In another embodiment of the invention, Ze is determined from changes in reflectance R caused by exercise, which affects Ze but not Zi. If R is determined once when Ze is high, and once after exercise where Ze is low, Ze can be determined from equation (9).

Figure 9:
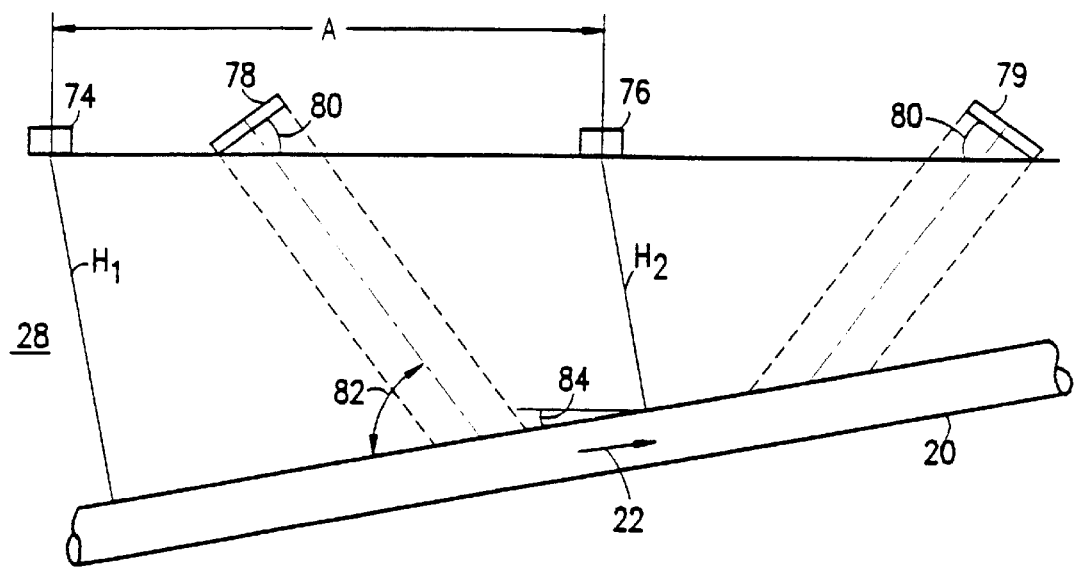
FIG. 9 is a schematic side view of apparatus for determining an incidence angle between ultrasonic beams, used for blood velocity measurement, and a blood vessel.

As described above, the error in velocity determination is quite low in many cases even if the incidence angle between blood vessel 20 and the various ultrasonic beams is not known. However, in a preferred embodiment of the invention, the incidence angle is measured and taken into account in the velocity determination and equation (2) is used. FIG. 9 is a schematic side view of apparatus for determining the incidence angle. A first transducer 74 measures a distance $H_1$ between transducer 74 and blood vessel 20 and a second transducer 76 measures a distance $H_2$ between transducer 76 and blood vessel 20. Since only times may be measured using transducers 74 and 76, the velocity or sound in soft tissue 28 must be estimated in order to determine distances $H_1$ and $H_2$. Alternatively, the soft tissue velocity is directly determined, using a method such as that described in PCT application PCT/IL96/121, titled "ULtrasonic device for determining bone characteristics" and filed on Oct. 3, 1996, the disclosure of which is incorporated herein by reference. Preferably, a very short pulse is used for distance determination, such as a 0.2 $\mu$ pulse repeated every 400 microseconds. A slope 84 can be determined from the difference between distances $H_1$ and $H_2$ and from a known (and preferably fixed) distance A between transducer 74 and transducer 76. A Doppler transducer 78 and a Doppler transducer 79 are both oriented at a known angle 80 relative to the line connecting transducers 74 and 76. Utilizing knowledge of slope 84, the incidence angle 82 of the Doppler beam from transducer 78 can be accurately determined. It should be appreciated that only one Doppler transducer is needed to accurately determine the velocity of flow 22, since incidence angle 82 is accurately known.

In a preferred embodiment of the invention, the acoustic attenuation of soft tissue 28 is determined and used to correct artifacts in the Doppler-shifted spectrum, which artifacts are caused by beam attenuation. A preferred method of determining the soft tissue attenuation uses an embodiment similar to that shown in FIG. 9. The attenuation per soft tissue unit length can be determined by comparing the attenuation along the known paths $H_1$ and $H_2$. The following equation derives $B_0$ (the attenuation per unit length) from attenuations $B_1$ and $B_2$ which are found along $H_1$ and $H_2$ respectively:

$$B_0 = 20 * \log \frac{B_2/B_1}{H_2 - H_1} \qquad (11)$$

If a broad band ultrasound system is used, the attenuation determination is repeated for several frequencies, to determine the attenuation in the tissue at each frequency.

A common problem with ultrasonic pencil beams is the spreading of the ultrasonic beams. In a preferred embodiment of the invention the ultrasonic transducers generate focused ultrasonic beams, as known in the art. Alternatively or additionally, the Doppler spectra are corrected for the intensity-non-homogeneity of the ultrasonic beams. For example, a circular transducer typically generates a beam which has a cross-section of (approximately) a two-dimensional Guassian. Further alternatively or additionally to correcting the spectra, the ultrasonic transducers are driven in a spatially non-uniform manner. However, these two types of correction for non-homogeneity are usually difficult to implement.

A non-homogeneous beam affects the accuracy in determining the average velocity. However, the maximum velocity is substantially unaffected, so the average velocity may be reproduced from the maximum velocity. Typically, the volume velocity is determined from the average velocity and the radius of vessel 20. This assumes that vessel 20 has a circular cross-section, however, in an imaging embodiment of the invention, as described below, the cross-section of vessel 20 can be determined and used instead of the radius. If the cross-section of vessel 20 is an ellipse, due to an off-axis viewing, the cross-section can be computed using a calculated incidence angle.

It should be appreciated that the walls of vessel 20 reflect more ultrasonic signal than the blood flow 22 itself. However, the velocity of the vessel walls is much lower than the blood velocity, so the contribution of the vessel walls to the Doppler-shifted spectrum is at the low values of Δf and can be filtered out using methods known in the art. Alternatively or additionally, the movement of the vessel walls is determined using a perpendicularly oriented ultrasonic sensor, such as shown in FIG. 6A.

When the flow in vessel 20 is smooth, the direction of flow 22 is generally along the long axis of vessel 20. However, near stenoses and in other cases the flow in vessel 20 is turbulent, resulting in a flow component which is normal to the wall of vessel 20. The turbulent flow adds a significant amount of noise signal to the Doppler spectrum and affects the distributions of velocities in vessel 20. In a preferred embodiment of the invention, the amount of turbulent flow is measured using an ultrasonic Doppler sensor which is perpendicular to the long axis of vessel 20, for example as shown in FIG. 6A. Preferably, a Doppler spectrum used for determining flow 22 is corrected using the measurement of the turbulence level. For example, by measuring the turbulence flow using a Doppler sensor perpendicular to the vessel flow direction and subtracting this measured flow from the non-perpendicular Doppler spectrum. Usually such correction take into account the incidence angle of the ultrasound beams on the vessel. It should be appreciated the turbulence level of the flow is clinically important, as it may indicate the smoothness of vessel 20 and/or blockage therein.

Figure 10A:
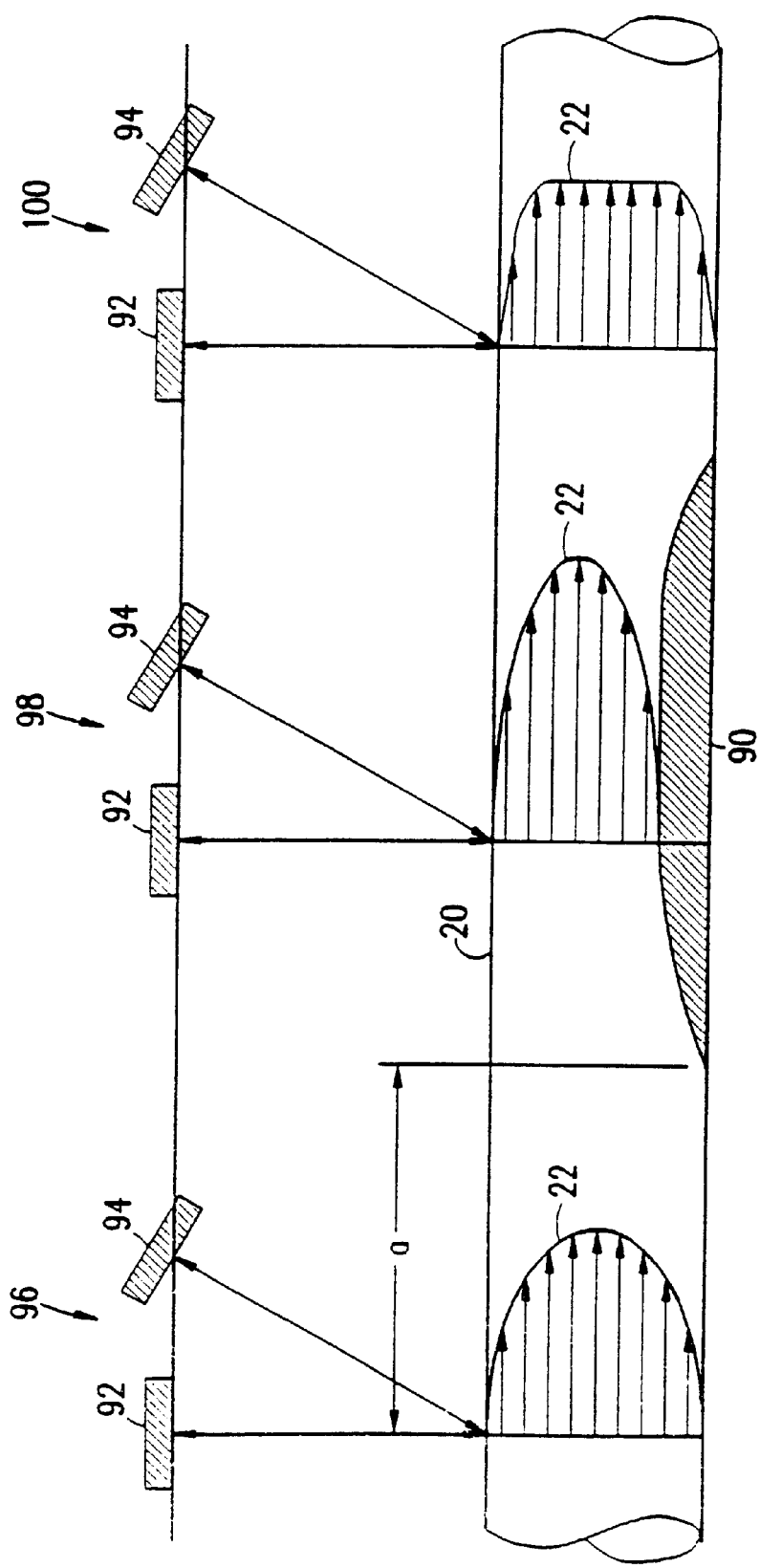

FIGS. 10A–D show the effect of a stenosis 90 on flow 22 in vessel 20. FIGS. 10B, 10C and 10D show the haemodynamic properties measured at a point 96 upflow from stenosis 90, at a point 98 at stenosis 90 and at a point 100 downflow from stenosis 90. At point 96 (FIG. 10A), a transducer 92 measures the diameter of vessel 20 and a transducer 94 measures the Doppler spectrum of flow 22. For purposes of illustration, only one transducer 94 is shown in FIG. 10A, however, preferably one or more than one are used to measure flow. FIG. 10B shows various haemodynamic properties of flow 22 graphically as a function of time. A graph 102 shows the unfilted Doppler spectrum, a graph 104 shows the diameter of vessel 20; and a graph 106 shows the velocity of flow 22. A shaded portion 108 in graph 106 represents loss of flow velocity caused by the reflection of the pulse wave by stenosis 90. A peak 110 represents a velocity increase caused by the reflection of the stenosis reflection by the Aortic valve. The pulse wave is also reflected by the end of the blood vessel (the furthest capillaries). The end reflection is also reflected by the Aortic valve and appears as a peak 112 in graph 106.

FIG. 10C shows the haemodynamic properties measured by transducers 92 and 94 at point 98, i.e., at stenosis 90. A graph 114 shows the unfitted Doppler spectrum, which, as a result of the narrowing of vessel 20, indicates a higher flow velocity than graph 102. A graph 118 shows the blood flow velocity, in particular, only a reflection of the end reflection is indicated as a peak 120.

FIG. 10D shows the haemodynamic properties measured by transducers 92 and 94 at point 100, downstream of stenosis 90, where flow 22 is typically turbulent. Thus, a graph 122, which shows the unfilted Doppler spectrum, is more irregular than graphs 102 and 114. In particular, a peak which corresponds to the flow normal to the long axis of vessel 20 may be indicated in graph 122 as a peak 124', if the turbulent velocity is faster than the general blood Sow, or as a peak 124", if the turbulent flow is generally slower than the general blood flow. A graph 128 show the flow velocity as a function of time. Most notably, peak 130 is wider than corresponding peaks in graphs 106 and 118 due to the turbulence.

Thus, stenoses can be found by determining changes in measured haemodynamic parameters. Also, stenoses usually cause a pressure drop, which can be determined by measuring the local blood pressure upflow and downflow of the stenosis. A calcified vessel may be identified by the profile of diameter changes that such a vessel has in response to a pulse wave. In addition, the flow in calcified vessels is usually slightly turbulent.

Another indicator for stenoses is the laminarity of the flow, which can be determined from the Doppler-shifted spectrum. A Doppler-shifted spectrum of laminar flow has a rectangular shape, such as shown as reference 102 in FIG. 10B (up to η=0.4). An example of a Doppler-shifted spectrum of non-laminar flow is shown in FIG. 10D, as reference 12.

Figure 11A:
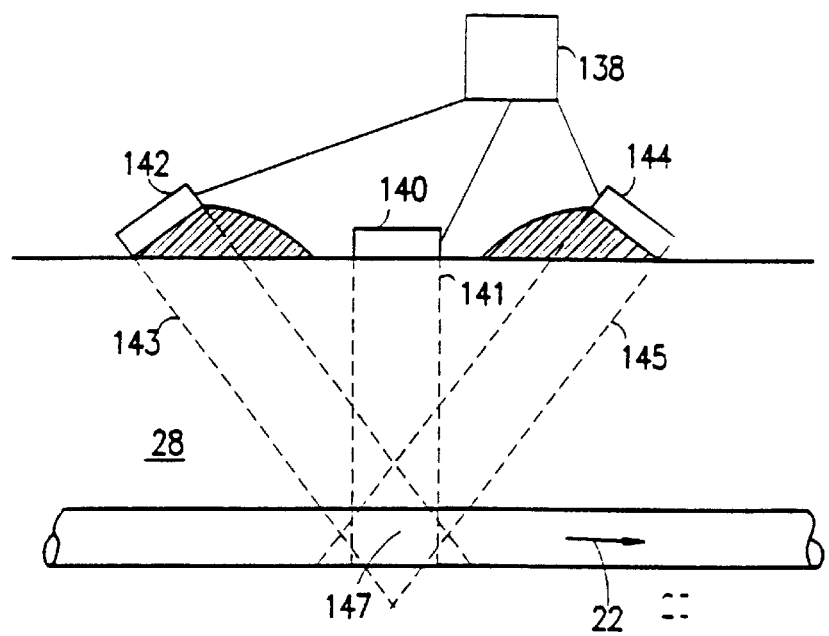
FIGS. 11A–C show schematic side views of a three-element flowmeter according to preferred embodiments of the invention.

FIG. 11A shows a three element flowmeter according to another preferred embodiment of the invention. The flowmeter includes a single transmitter 140 which transmits along a transmission path 141 to blood vessel 20, a receiver 142 which receives along a reception path 143 and a receiver 144 which receives along a reception path 145. A controller 138 controls transmitter 140 and receivers 142 and 144. Only one transmitter is necessary because reception path 143 and reception path 145 both intersect transmission path 141 at blood vessel 20. Preferably, reception path 143 and reception path 145 intersect with transmission path 141 at a single point 147 in vessel 20. Alternatively or additionally, path 141 is a wider angle lobe than as preferred in other embodiments of the invention. However, using a fan beam generally reduces the accuracy of the velocity determination.

In an alternative embodiment of the invention, a well known equivalence between transmitters and receivers is used, so transmitter 140 is replaced by a receiver and receivers 142 and 144 are replaced by transmitters. Interaction between the two transmitted beams may be minimized by utilizing different frequencies for each transmitter or by time-multiplexing the transmitters.

Figure 11B:
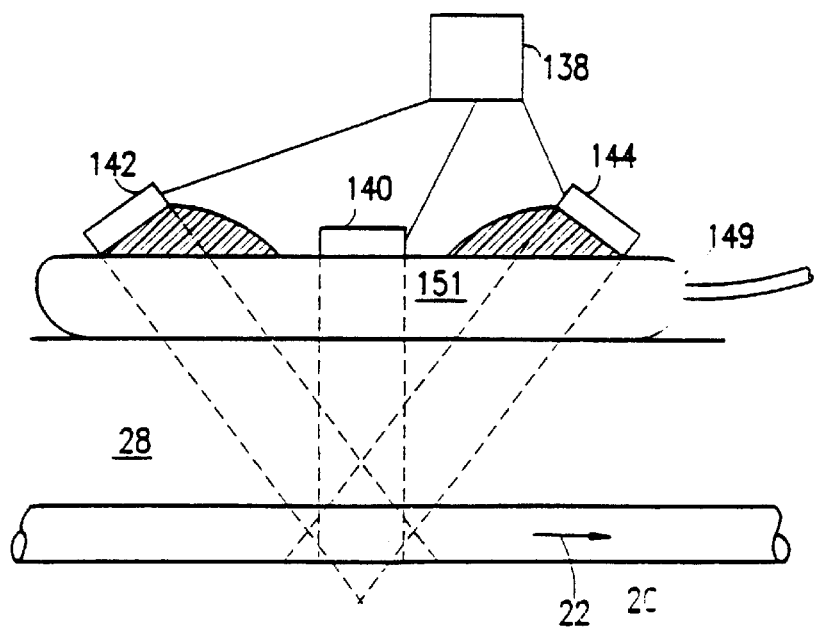

As can be appreciated, in a rigid flowmeter, such as shown in FIG. 11A, a particular configuration of paths 141, 143 and 145 is only optimal for measuring blood flows at a single depth. FIG. 11B shows an inflatable spacer 149 according to a preferred embodiment of the invention. An ultrasonic coupling material 151 is injected into spacer 149 until a desired distance between the flowmeter and blood vessel 20 is achieved. Alternatively, spacer 151 is one of a set of spacers having different, set, thicknesses.

Figure 11C:
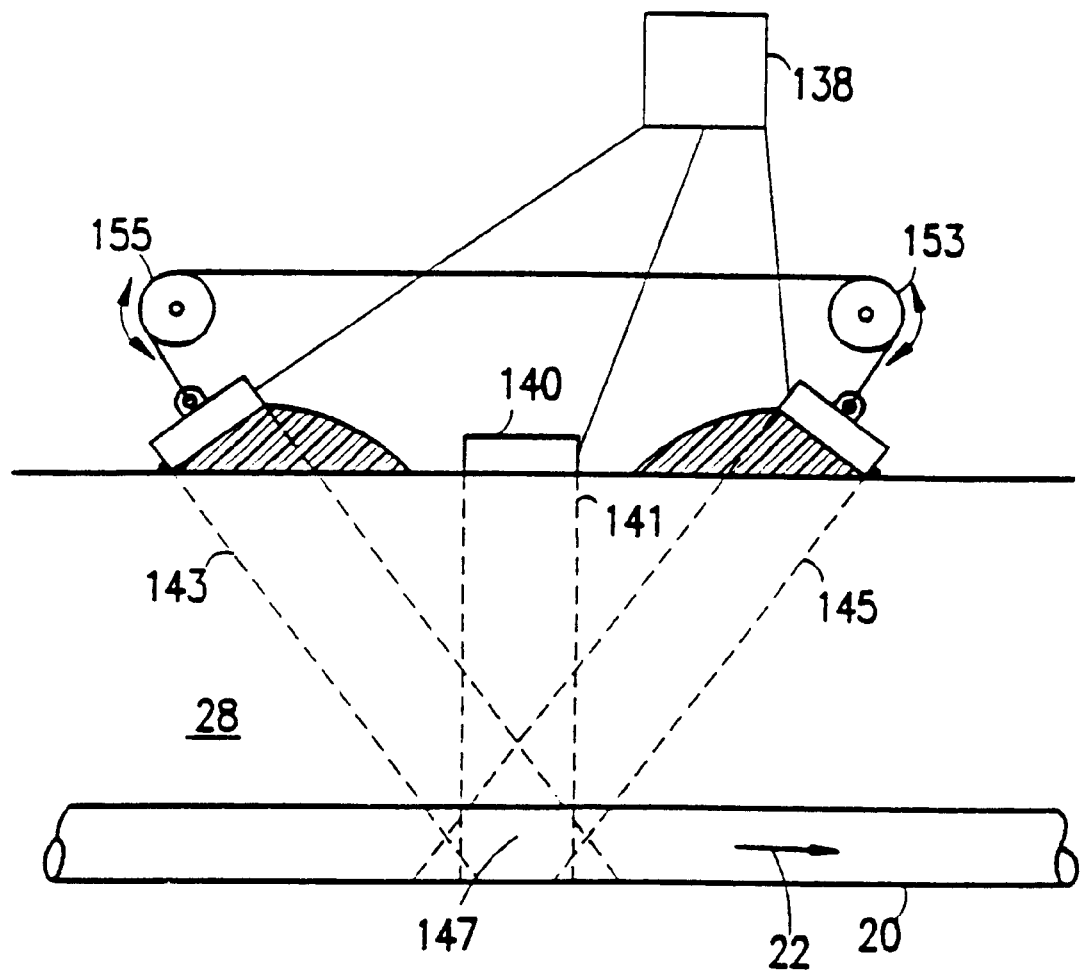

FIG. 11C shows an orientation changing apparatus according to a preferred embodiment of the invention. A rotator 153, connected to receiver 144 and a rotator 155, connected to receiver 142 are coupled so that both receivers have equal and opposite changes of orientation. As a result, the intersection of paths 143 and 145 is always in path 141. Rotating rotators 153 and 155 results in relative movement between the intersection point and transmitter 140.

The intersection of the ultrasonic beams with vessel 20 can be determined by analyzing Doppler-shifted reflections of the beams, as described below, or by estimating the depth of vessel 20.

Figure 12A:
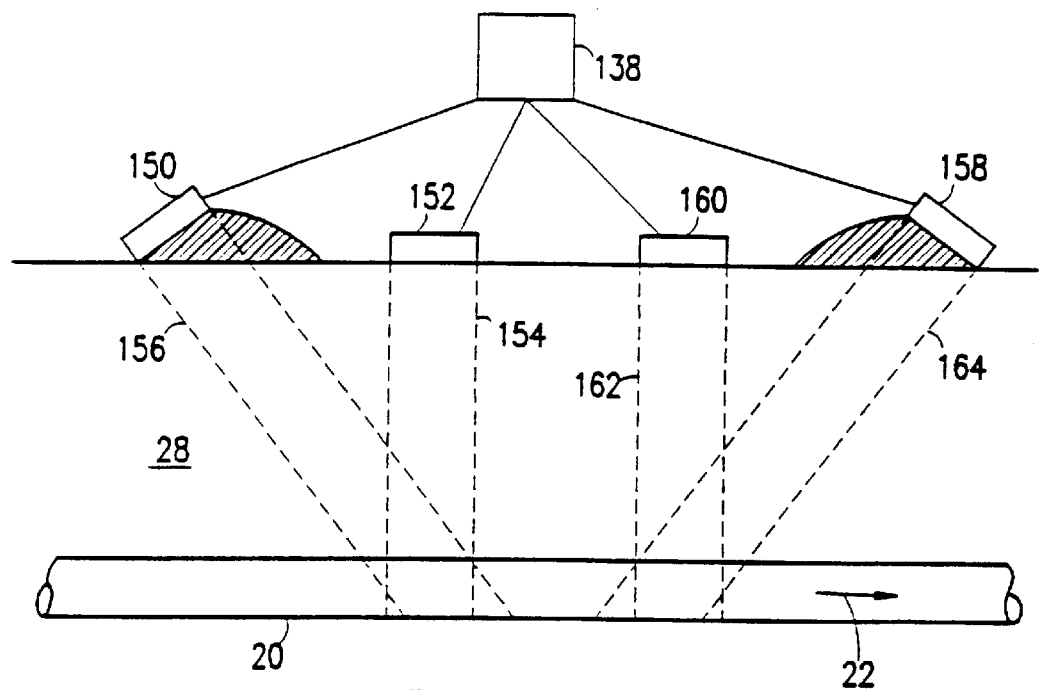
FIGS. 12A–C show schematic side views of four-element flowmeter according to preferred embodiments of the invention.
Figure 12B:
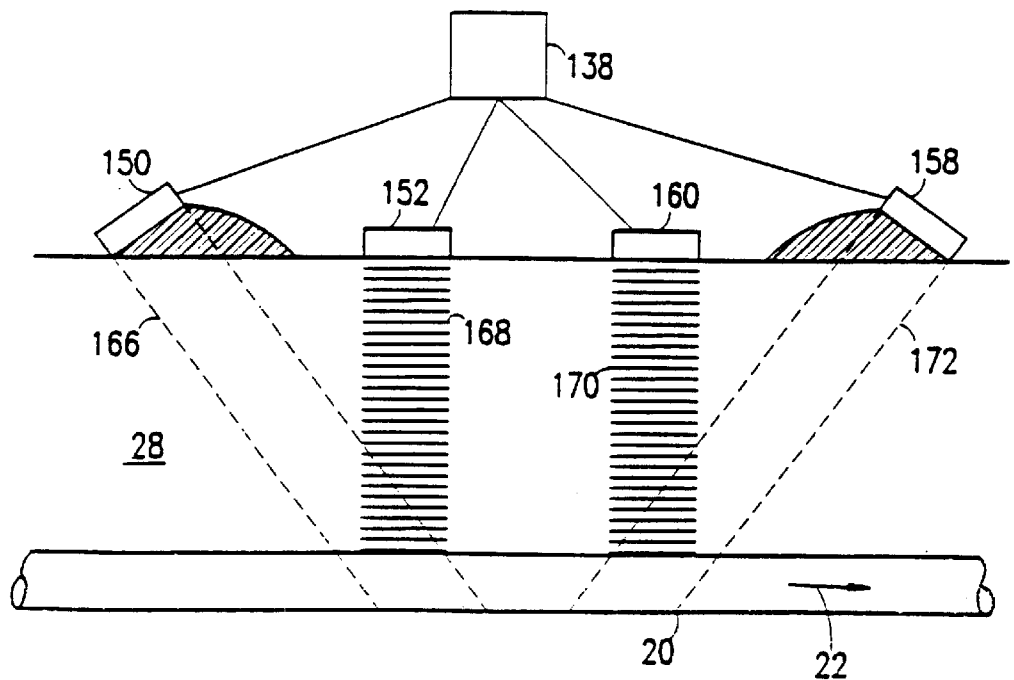
Figure 12C:
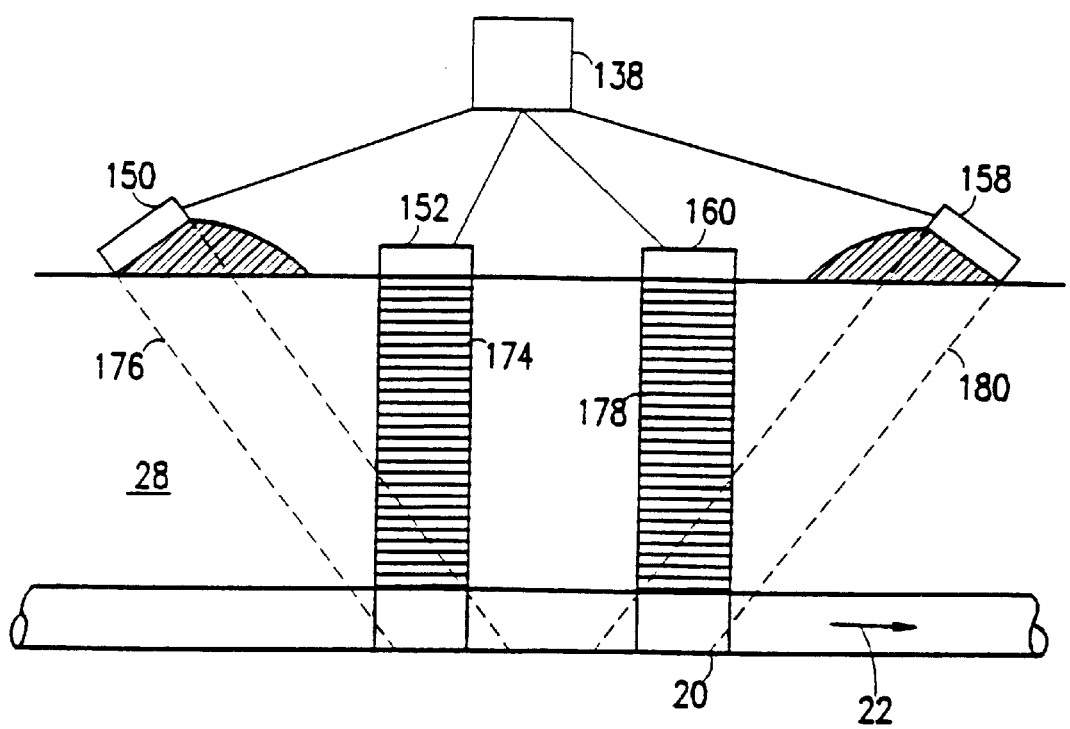

FIGS. 12A–12C show various four-element ultrasound flowmeters according to preferred embodiments of the invention. The flowmeters of FIGS. 12A–12C all comprise four transducers 150, 152, 158 and 160 which are controlled by a controller 138. However, various transmission and reception protocols are utilized to achieve different effects. The flowmeter of FIG. 12A organizes the transducers into two transmitter/receiver pairs, to reduce noise generated when the same ultrasonic element is used for both transmitting and receiving. Thus, transducer 150 and transducer 152 comprise a first pair, in which an ultrasonic beam is transmitted from transducer 150 to vessel 20 to have a direction component in the general direction of flow 22 and transducer 152 receives the Doppler-shifted signal from vessel 20. Transducers 158 and 160 operate in a similar manner albeit in a direction opposite of flow 22. Thus, this embodiment is functionally equivalent to the embodiment of FIG. 1C.

The flowmeter of FIG. 12B organizes the transducers so that each transducer receives a Doppler-shifted reflection of its own transmission. Spaced apart transducers 152 and 160 are used to determine the pulse wave velocity, changes in the diameter of vessel 20 and/or turbulence, as described above with reference to FIGS. 6A and 6B. Transducers 150 and 158 are used to determine the velocity of flow 22, as described with reference to FIGS. 1A–1C.

The flowmeter of FIG. 12C organizes the transducers so that transducers 150 and 158 are used only to detect Doppler-shifted reflections from flow 22. Transducers 152 and 160 are used both as transmitters for transducers 150 and 158, as in FIG. 12A and as vessel diameter determiners, etc., as in FIG. 12B. Thus, when transducer 152 transmits a beam 174 towards vessel 20, one reflection is detected by transducer 152 itself, and a reflection 176, which is Doppler-shifted by flow 22, is detected by transducer 150.

In the flowmeters of FIGS. 12A–12C, transducers 152 and 160 are preferably oriented to have parallel transmission/reception directions. Thus, the flowmeters can be aligned so that ultrasonic beams from both transducers are perpendicular to flow 22. However, it is not essential that the beams be precisely perpendicular to the flow. Pulse wave velocity is determined with the same accuracy whether or not the beams are perpendicular to flow 22, as long as they are parallel to each other. Errors in measuring changes in the vessel diameter can be corrected for utilizing the incidence angle, which can be determined as described above. It should be appreciated that a single four-element flowmeter can be sequentially activated using various ones of embodiments shown in FIGS. 12A–12C. It should be appreciated, that the diameter is preferably determined using a pulse ultrasound sequence, and the flow is preferably determined using continuous ultrasound waves.

Figure 13A:
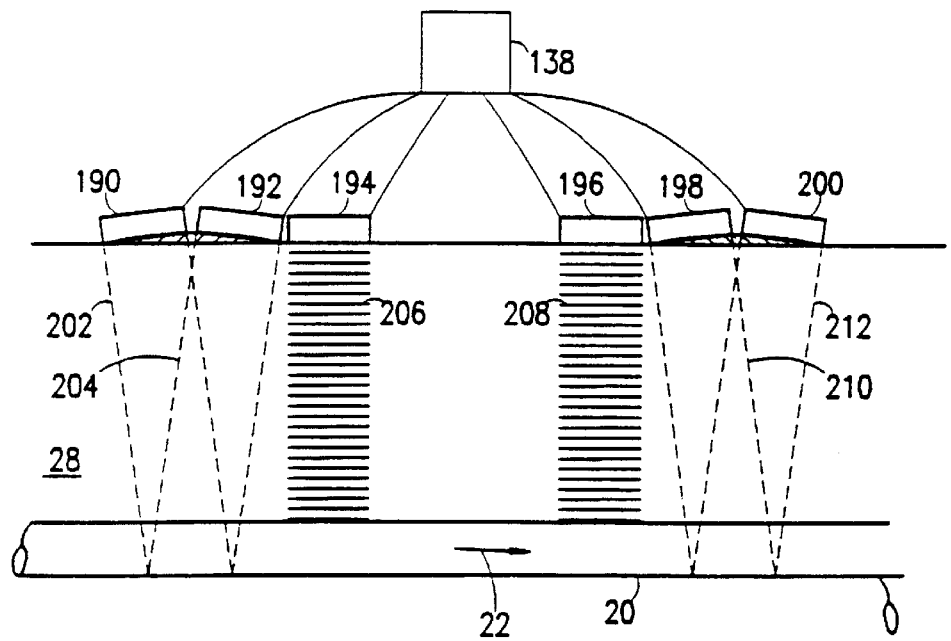
FIG. 13A is a schematic side view of a six-element flowmeter according to a preferred embodiment of the invention.
Figure 13B:
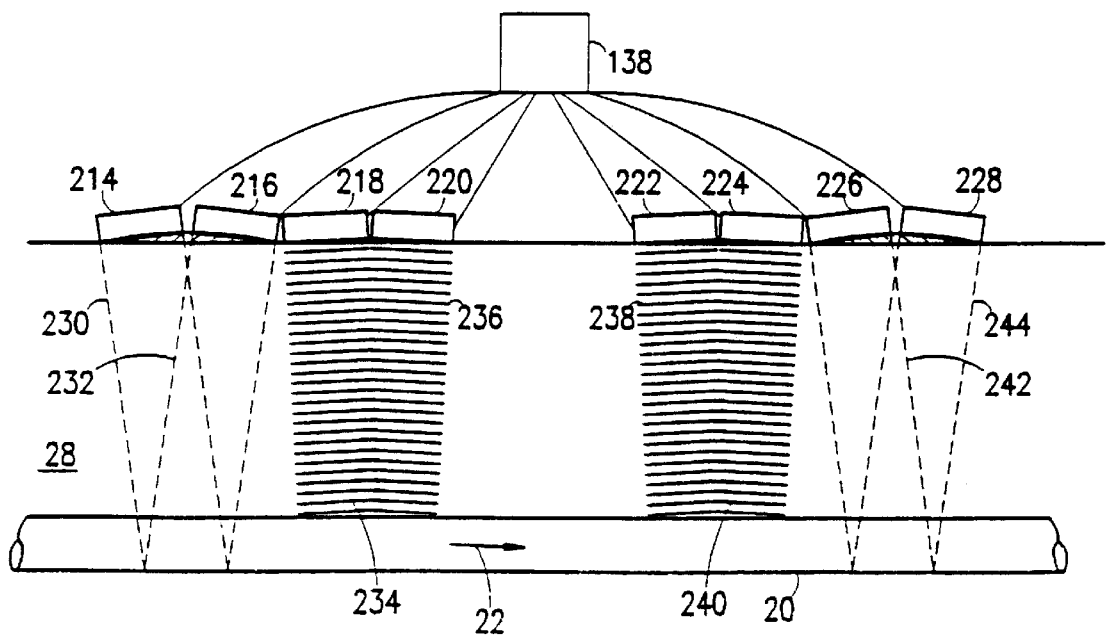
FIG. 13B is a schematic side view of an eight-element flowmeter according to a preferred embodiment of the invention.

FIGS. 13A–13B show additional flowmeters according to preferred embodiments of the present invention. FIG. 13A shows a six-element flowmeter in which a transducer 194 and a transducer 196 each determine changes in the diameter of vessel 20, as described above. A pair of transducers 190 and 192 (and a pair 198 and 200) are activated by controller 138 as a transmitter/receiver pair for determining the velocity of flow 22, as described with reference to FIG. 1C and FIG. 12A. FIG. 13B shows a eight element flowmeter in which a pair of transducers 218 and 220 (and a pair 222 and 224) are activated as a transmitter/receiver pair to determine changes in the diameter of vessel 20. A pair of transducers 214 and 216 (and a pair 226 and 228) are activated as a transmitter/receiver pair for determining the velocity of flow 22.

FIG. 14A is a schematic diagram of an ultrasonic generator which can be used for the activation of ultrasonic transmitters in the above described embodiments. A particular feature of the generator is a low-noise high-stability output. A low-current low-noise ultrasound generator 250 generates a sine wave signal at a desired output frequency. FIG. 14B shows the output of such a generator. A low saturation amplifier 252 amplifies the signal and, due to its low saturation, flattens the sine wave. FIG. 14C show a quasi-square wave signal which is the result of amplifying the signal of FIG. 14B using amplifier 252. It should be appreciated, that most of the noise in the signal of FIG. 14C is located in the vertical portions of the square wave, where it does not have much effect on the reflected Doppler-shifted spectrum. The signal which reaches the detector is a clean sinusoidal, since the ultrasound transducer absorbs all the harmonics.

Figure 15:
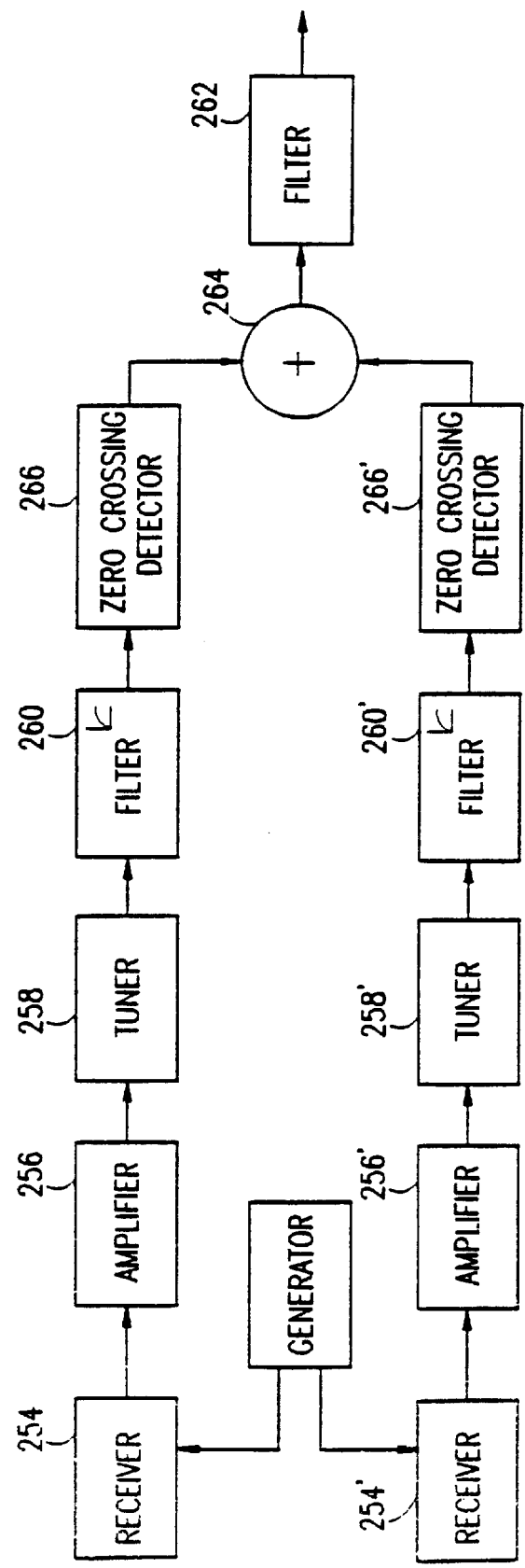
FIG. 15 is a schematic diagram of a zero-crossing detector, according to a preferred embodiment of the invention.

FIG. 15 is a schematic block diagram illuminating a preferred method of determining the velocity from the Doppler-shifted spectrum. An output signal from a receiver 254 is amplified by an amplifier 256 which also removes the transmitted frequency and is stepped down in frequency by a tuner 258. Preferably, tuner 258 is a super-heterodyne tuner. Tuner 258 may also step up the frequency if it is desired. A filter 260 then filters the signal in a frequency-dependent manner so that high frequencies are emphasized more than low frequencies. The number of zero-crossings are then counted by a zero crossing counter 266. As described above, two channels are used, one having a positive Doppler-shift and one having a negative Doppler-shift (marked with an apostrophe), so that alignment errors are compensated for. The sum of zero-crossings is directly related to the quadric-average velocity. Thus, the average or maximum velocities can be determined using the known ratio between various velocities.

Alternatively to combining the two channels in the velocity domain, the two channels may be combined in the frequency domain or in the time domain.

In pulsile flow, the apparatus in FIG. 15 should be adapted to detect when the direction of the flow is reversed from its usual direction, so that a correct flow direction may be attributed to the flow.

In a preferred embodiment of the invention, the velocity of flow 22 is determined using a continuous wave ultrasound signal. Alternatively, a pulsed ultrasound regime is used. A preferred ultrasonic frequency for flow velocity determination and for detection of movement of vessel walls is 3–10 MHz. Referring to FIG. 1C, if ultrasonic beams 26 and 32 overlap in time as well as space, transducer 24 might pickup reflections of beam 32, in addition to reflections from beam 26. Thus, beams 26 and 32 are preferably staggered either in the time domain, the frequency domain or in space, so that they do not intersect at vessel 20.

As can be appreciated, a flowmeter as described herein above is preferably aligned with blood vessel 20 before the velocity of flow 22 is determined. The flowmeter is typically an elongated rigid object, so for a flowmeter to be correctly aligned with a vessel, the entire length of the flowmeter must be parallel to the vessel and the transmission direction of the flowmeter must be co-planar with the flowmeter and the vessel.

Referring to FIG. 1A, the orientation of vessel 20 may be visually or tactilely determined in some main veins and arteries, such as, the Femoral and Carotid arteries and the Jugular veins. Alternatively, an audio or visual display of signals detected by transducer 24 can be used to determine whether beam 26 intersects an artery, a vein or neither. An operator can orient the flowmeter at different orientations until both transducer 24 and transducer 30 exhibit similar output signals. Alternatively, transducers 24 and 36 can be phased-array scanners which automatically scan tissue 28 to find Doppler-shifting flow 22. Preferably, an estimated depth of vessel 20 is known and a flowmeter which is adapted for that depth is used. Alternatively, the orientation of beams 26 and 32 may be controlled mechanically, as for example in FIG. 11C, or electronically, such as when transducers 24 and 30 are phased arrays.

In a preferred embodiment of the invention, the flowmeter is oriented so that the Doppler-shifted spectrum detected by transducer 24 is substantially similar to the spectrum detected by transducer 30. In such a case, $\gamma=0$. Alternatively, the flowmeter is oriented so that beam 26 is substantially perpendicular to flow 22, so the incidence angle is equal to $90-\theta$ and is, thus, known.

During normal operation, an operator may desire not to determine velocity at portions of blood vessels which are obstructed by stenosis. A stenosis may be detected as described above with reference to FIGS. 10A–D and the flowmeter moved to a different location.

An interesting result of the laminarity of flow 22 is that if the ultrasonic beam intersects at least half the width of vessel 20, the entire Doppler-shifted spectrum can be reproduced. Thus, an exact overlap between the ultrasonic beam and vessel 20 is not necessary.

In some preferred embodiments of the invention, linear FM modulated signals or pulse signals are used to determine the velocity of flow 22. Such signals can also be used to perform range clipping on reflected signals so that only signals from a particular blood vessel at a particular distance are taken into consideration.

Figure 16A:
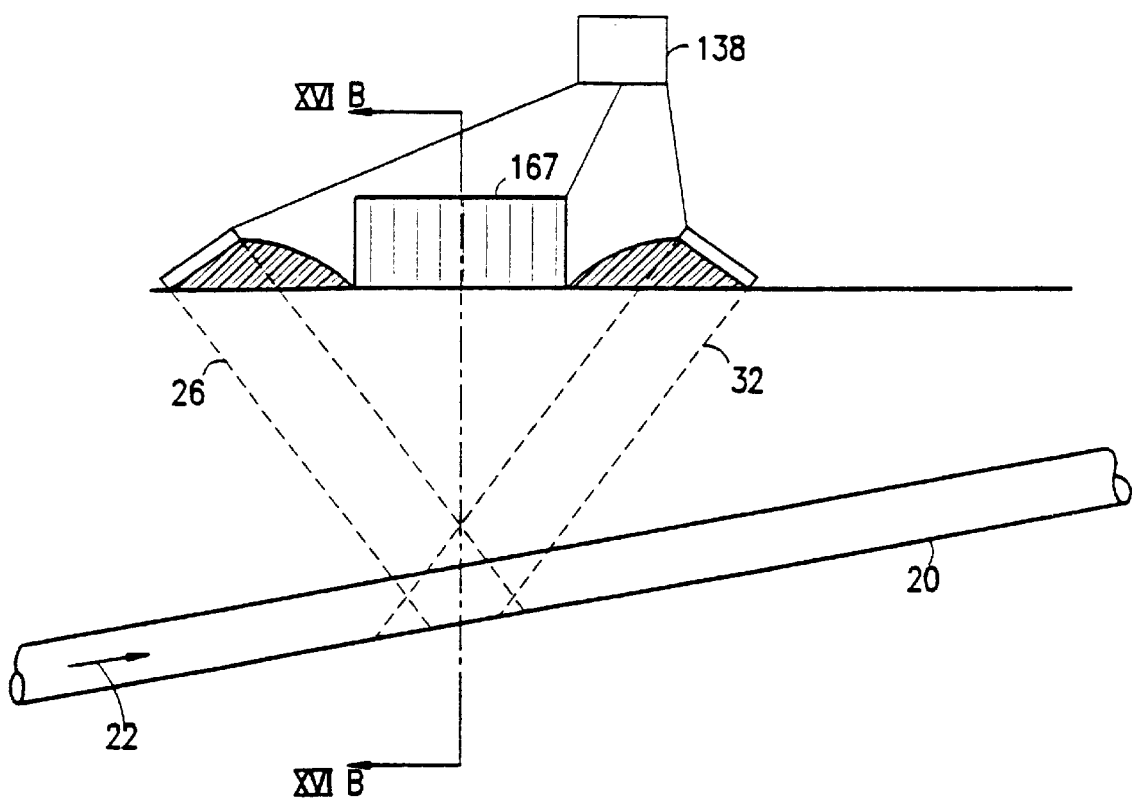
FIG. 16A shows a side view of a flowmeter having an imaging sensor, according to a preferred embodiment of the invention.
Figure 16B:
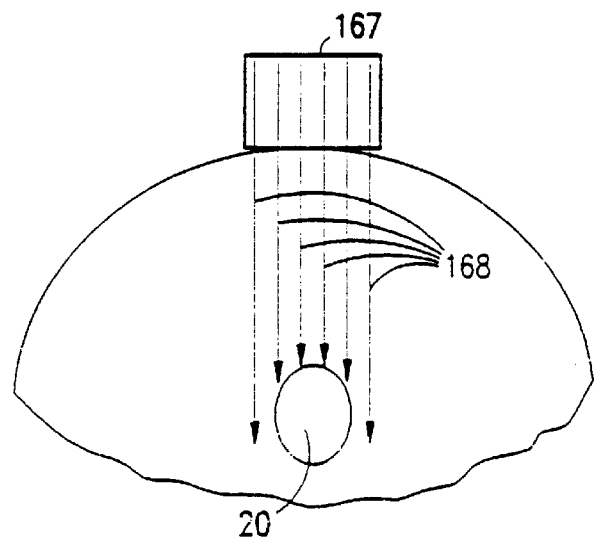
FIG. 16B is a cross-section view of FIG. 16A, along cut XXVIB—XXVIB.

FIG. 16A shows a flowmeter, such as shown in FIG. 1A, incorporating an imaging sensor 167, which can be used to detect whether beams 26 and 32 straddle vessel 20. FIG. 16B shows a cross-section of vessel 20 and a plurality of beams 168, from sensor 167, which straddle vessel 20. Sensor 167 may be a one or two dimensional imaging sensor, in addition sensor 167 may be a phased array type scanning sensor or a multiple beam scanning sensor, as shown in FIG. 16B. No image output is necessary for sensor 167, rather intersection with vessel 20 can be detected automatically by controller 138.

Figure 17:
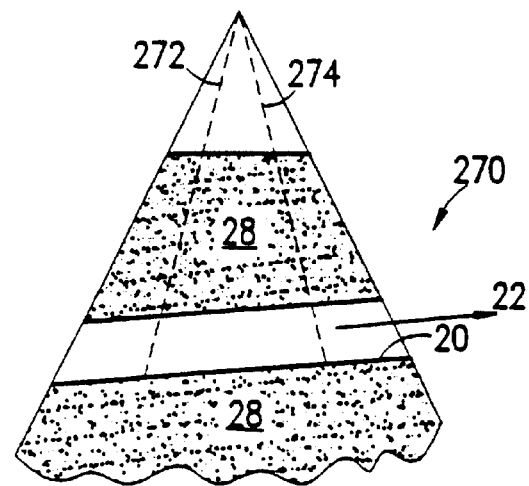
FIG. 17 shows a slice of an ultrasonic image generated by an ultrasonic imager.

In a preferred embodiment of the invention, methods, as described herein, are practiced using existing ultrasonic imaging equipment. FIG. 17 shows an image slice 270, such as produced by an ultrasonic imaging sensor. An ultrasound beam 272 and an ultrasound beam 274, both of which are used to acquire image 270, can also be used to practice various embodiments of the present invention. For example, a Doppler-shifted spectrum of beams 272 and 274 can be acquired by the ultrasonic imaging sensor and the velocity of flow 22 can be determined as described hereinabove. In this way alignment of the beams with the vessel can be easily achieved.

Figure 18:
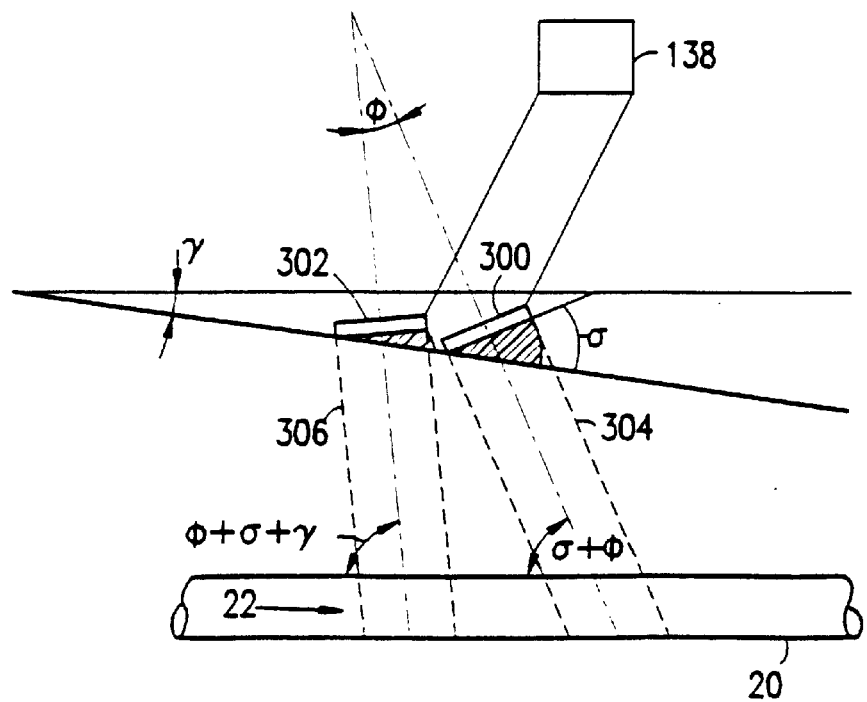
FIG. 18 is a schematic diagram showing a flowmeter according to a preferred embodiment of the present invention using two ultrasonic beams, both of which have direction components in the same direction relative to a measured flow.

Another preferred embodiment of the invention provides a method of determining the incidence angle of an ultrasonic beam and a blood vessel, using two angled ultrasonic beams having direction components with the same orientation relative to flow in the vessel. FIG. 18 shows a flowmeter comprising a first transducer 300, which transmits an ultrasonic beam 304 to vessel 20 and a second transducer 302 which transmits an ultrasonic beam 306 toward vessel 20. The angle between beams 304 and 306 is indicated as an angle $\phi$. Beam 304 is transmitted at an Angle $\beta$ relative to the surface of tissue 28, however, if vessel 20 is at an angle $\gamma$ to the surface, the incidence angle of beam 304 is $\sigma+\gamma$. The following equations can be used to determine $\gamma$ and, thus, a velocity V of flow 22. In the following equations, φ+σ are written as θ, $F_4$ represents the maximum Doppler-shift of beam 304 and $F_6$ represents the maximum Doppler-shift of beam 306:

$$F_4 = \frac{2v}{\lambda}\cos(\sigma + \gamma) = \frac{2v}{\lambda}(\cos\sigma\cos\gamma - \sin\sigma\sin\gamma) \quad (12)$$

$$F_6 = \frac{2v}{\lambda}\cos(\theta + \gamma) = \frac{2v}{\lambda}(\cos\theta\cos\gamma - \sin\theta\sin\gamma) \quad (13)$$

After extracting γ:

$$\gamma = \arctan\frac{F_6 \cdot \cos\sigma - F_4\cos\theta}{F_6 \cdot \sin\sigma - F_4 \cdot \sin\theta} \quad (14)$$

Velocity v can easily be determined from equation (12) as:

$$v = \frac{\lambda \cdot F_4}{2 \cdot (\cos\sigma\cos\gamma - \sin\sigma\sin\gamma)} \quad (15)$$

When applying methods of the present invention using a scanning ultrasound device a large number, n, of beams can be incorporated to determine velocity v. The following equation can be used, with n beams with direction components in the same direction relative to the flow, to determine $\gamma_n$, where $F_n$ is the Maximum Doppler-shifted frequency of beam n:

$$\gamma_n = \arctan\frac{F_{n+1}\cos\sigma_{n+1} - F_n\cos\sigma_n}{F_{n+1}\sin\sigma_{n+1} - F_n\sin\sigma_n} \quad (16)$$

A more precise estimate of γ may be determined by averaging:

$$\gamma = \frac{1}{n}\sqrt{\sum_{i=1...n}\gamma_i^2} \quad (17)$$

And velocity v is:

$$v = \frac{\lambda}{2n}\sum_{i=1...n}\frac{F_n}{\cos\theta_n\cos\gamma_n - \sin\theta_n\sin\gamma_n} \quad (18)$$

Figure 19A:
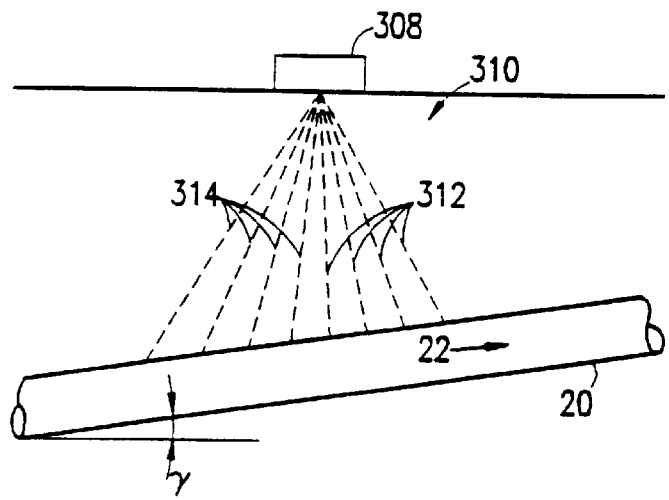
FIG. 19A is a schematic diagram showing a flowmeter according to a preferred embodiment of the invention utilizing more than two ultrasonic beams to determine a flow velocity.
Figure 19B:
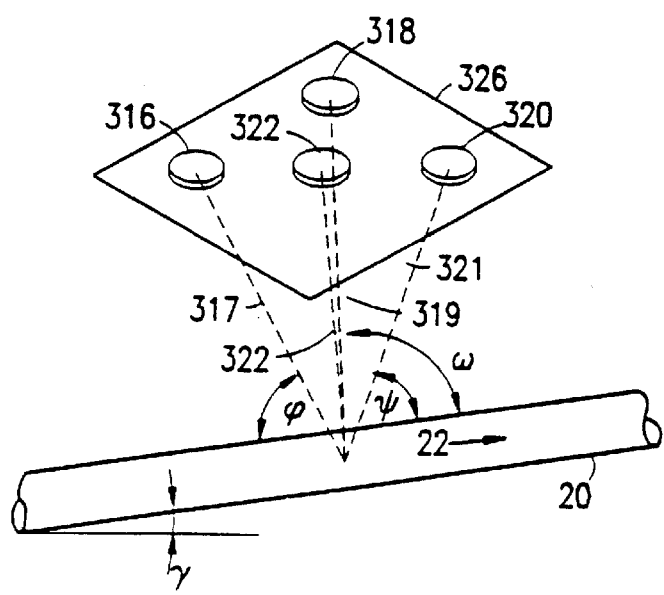
FIG. 19B is a schematic diagram showing a flowmeter according to a preferred embodiment of the invention in which three non-coplanar ultrasonic beams are used to determine a flow velocity.

FIG. 19A shows an ultrasound scanner 308 which transmits a plurality of beams 310 towards vessel 20. Beams 310 can be divided into a first group 312 of beams having a velocity component in the direction of flow 22 and a second group of beams having a velocity component in the opposite direction. In a preferred embodiment of the invention beams from group 312 are paired with beams from group 314, velocities determined as described above with reference to FIG. 1C, and the average of the velocities utilized as the velocity of flow 22. As can be appreciated, in an ultrasound scanners, the angles between the beams are known. If the number of beams in group 312 is smaller than the number of beams in group 314, some of the beams in group 312 can be paired twice. In an alternative preferred embodiment of the invention, γ is also determined. Thus, spectra of unpaired beams in group 314 can processed as regular Doppler-shifted spectra with a known incidence angle. It can be appreciated that with so many sources of data, very accurate results can be achieved Referring to FIG. 1A it should be appreciated that transducers 24 and 30 must lie in a same plane as vessel 20. If beams 26 and 32 do not intersect, rotating vessel 20 out of the plane will cause either beam 26 or beam 32 to miss vessel 20. However, if beams 26 and 32 intersect at vessel 20, the flowmeter can be rotated around a line connecting the intersection point and the flowmeter so that beams 26 and 32 are both perpendicular to vessel 20 and still intersect vessel 20. In such an orientation, no Doppler-shifting is achieved and the determined velocity is zero. In other, less extreme cases (beams are not perpendicular), the result is that an incorrect flow velocity is determined. FIG. 19B shows a flowmeter according to a preferred embodiment of the invention which automatically compensates for such rotations. Three transducers 316, 318 and 320 are arranged in a plane 326 so that a beam 317 from transducer 316, a beam 319 from transducer 318 and a beam 321 from transducer 320 all intersect at a location 324 in vessel 20. Optionally, a transmitter 322 transmits an ultrasonic beam towards location 324 and transducers 316, 318 and 320 act as receivers. The angle between beam 317 and vessel 20 (actually flow 22) is φ, between beam 319 and vessel 20 (actually flow 22), ω, and between beam 321 and vessel 20 (actually flow 22), ψ. An angle between plane 326 and vessel 20 (actually flow 22) is γ. The following equations express the relationship between the velocity v of flow 22 and maximum Doppler-shifted frequencies $F_n$, where $F_1$, $F_2$ and $F_3$ correspond to the maximum Doppler-shifted frequencies in transducers 316, 318 and 320 respectively:

$$F_1 = -\frac{2v}{\lambda}(\cos\varphi\cos\gamma - \sin\varphi\sin\gamma - \sin\gamma) \quad (19)$$

$$F_2 = \frac{2v}{\lambda}(\cos\omega\cos\gamma + \sin\omega\sin\gamma + \sin\gamma) \quad (20)$$

$$F_3 = \frac{2v}{\lambda}(\cos\psi\cos\gamma + \sin\psi\sin\gamma + \sin\gamma) \quad (21)$$

Thus:

$$F_2 - F_1 = \frac{2v}{\lambda}[\cos\gamma \cdot (\cos\varphi + \cos\omega) + \sin\gamma \cdot (\sin\omega - \sin\varphi)] \quad (22)$$

$$F_3 - F_2 = \frac{2v}{\lambda}[\cos\gamma \cdot (\cos\psi - \cos\omega) + \sin\gamma \cdot (\sin\psi - \sin\omega)] \quad (23)$$

$$F_3 - F_1 = \frac{2v}{\lambda}[\cos\gamma \cdot (\cos\psi + \cos\varphi) + \sin\gamma \cdot (\sin\psi - \sin\varphi)] \quad (24)$$

If φ is at least 70°, as is the case when transducers 316, 318 and 320 and location 324 form a pyramid with a small base, the terms "sinγ (sin( )-sin( ))" are close to zero and may be ignored, so:

$$F_2 - F_1 = \frac{2v}{\lambda}[\cos\gamma \cdot (\cos\varphi + \cos\omega)] \quad (25)$$

$$F_3 - F_2 = \frac{2v}{\lambda}[\cos\gamma \cdot (\cos\psi + \cos\omega)] \quad (26)$$

$$F_3 - F_1 = \frac{2v}{\lambda}[\cos\gamma \cdot (\cos\psi + \cos\varphi)] \quad (27)$$

The projections $V_1$, $V_2$ and $V_3$ of velocity v can be determined simply by:

$$V_1 = \frac{\lambda}{2}(F_2 - F_1) \quad (28)$$

$$V_2 = \frac{\lambda}{2}(F_3 - F_2) \quad (29)$$

$$V_3 = \frac{\lambda}{2}(F_3 - F_1) \quad (30)$$

And v is determined by:

$$v = \sqrt{V_1^2 + V_2^2 + V_3^2} \quad (31)$$

It should be noted that since γ is close to zero, it can be ignored. Alternatively, once V is calculated ignoring γ, γ can be calculated from any of equations (19)–(21), since V is known. It should also be noted that φ, ω and ψ can be determined from the geometry of transducers 316, 318 and 320. Preferably, the transducers are symmetrically disposed on a circumference of a circle. In addition, equation (31) can be simply expanded accommodate a system having n beams, using the same methods.

Figure 20A:
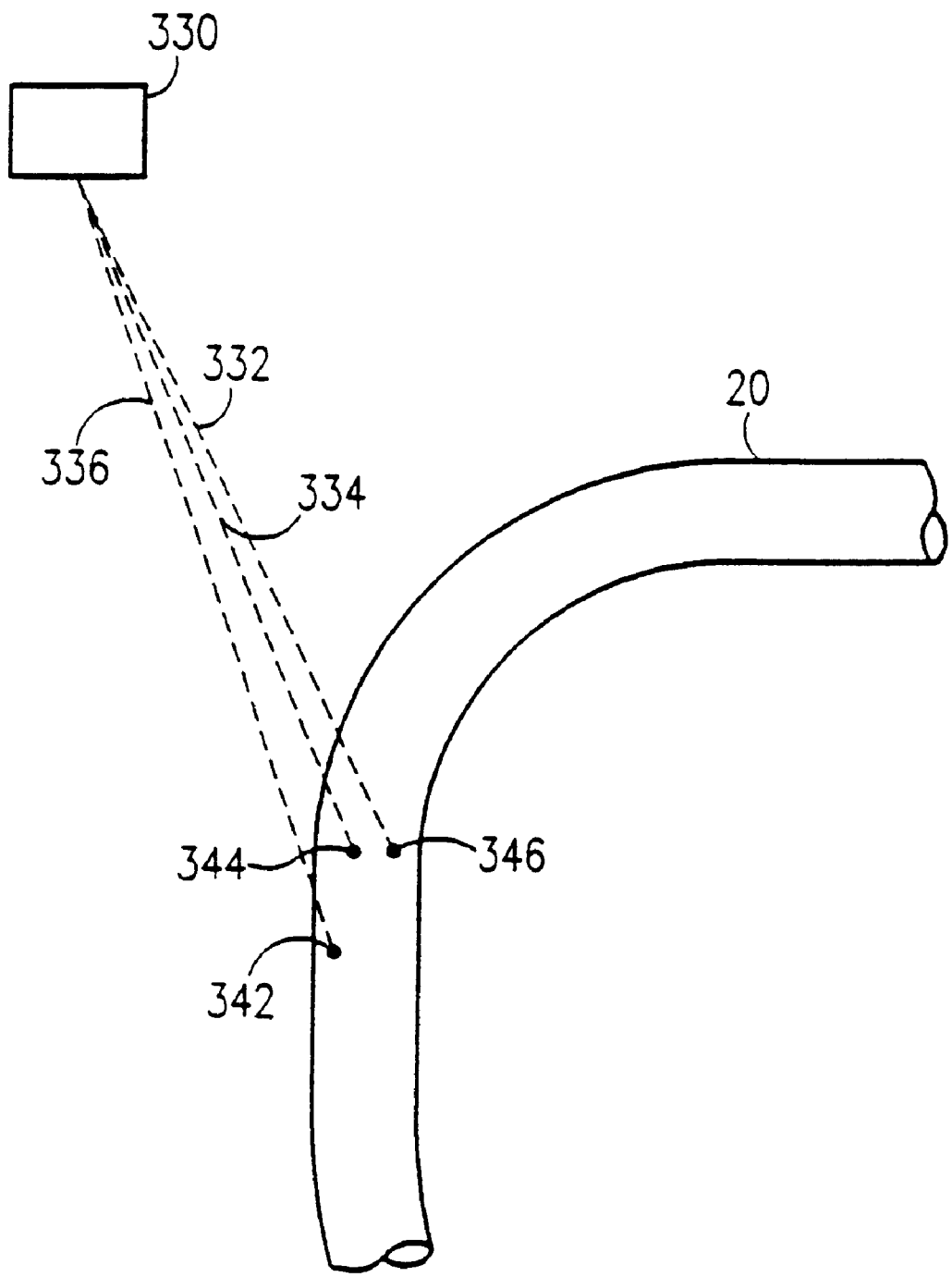
FIG. 20A shows a flowmeter for determining stroke volume, according to a preferred embodiment of the invention.

Another preferred embodiment of the invention related to determining the stroke volume of the left ventricle by determining flow in the aorta. One method of determining the stroke volume would be to perform the processing, as described above with reference to FIG. 17, on an image acquired during an echocardiography procedure. Alternatively, a flowmeter, such as described above, which has small dimensions can be guided into the digestive tract and urged against the wall of the esophagus to provide a direct ultrasonic line of sight between the flowmeter and the aorta. Outside of the body, there is only one location at which the aorta is ultrasonically visible without interference from ribs or lungs, namely the suprasternal notch. Using conventional Doppler-ultrasound devices, the flowmeter must be aligned with the direction of the flow in the aorta. Unfortunately, this alignment is difficult and painful for the patient. FIG. 20A shows a flowmeter according to a preferred embodiment of the invention, which does not have to be as precisely aligned. A transducer 330, which is placed over the suprasternal notch, transmits three ultrasonic beams, 332, 334 and 336 which intersect with an aorta.

Figures 20B, 20C:
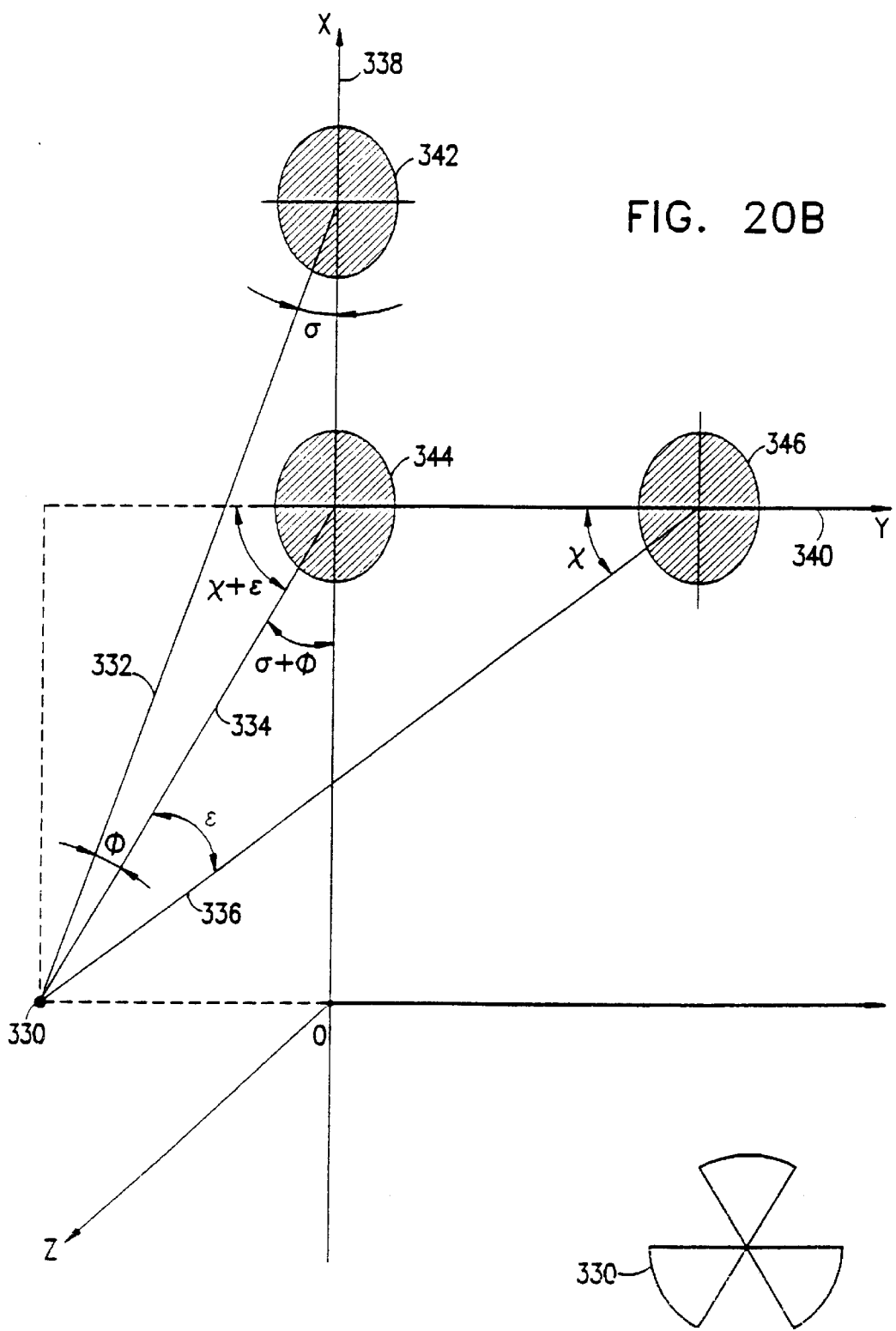
FIG. 20B is a diagram showing angles between ultrasound beams generated by the embodiment of FIG. 20A.
FIG. 20C is a schematic top view of an ultrasonic transducer preferred for the embodiment of FIG. 20A.

Unlike most blood vessels, the flow in the aorta is not laminar. Rather, the flow is turbulent and the flow velocity is approximately equal across the entire cross-section of the aorta. FIG. 20B is a diagram which shows one method of determining the velocity of the flow in the aorta, based on determining the incidence angle of the ultrasonic beams to the flow in the aorta and on acquiring a Doppler-shifted reflection from the blood in the aorta. In FIGS. 20A and 20B, reference numbers 342, 344 and 346 indicate the intersection locations of beam 332, beam 334 and beam 336, respectively, with the aorta. Velocity component $V_1$ is a projection of a velocity v, of the blood in the aorta, along an axis 338 which connects intersection locations 342 and 344. Likewise, velocity component $V_2$ is a second projection of v, along an axis 340 which connects locations 344 and 346. Velocity $V_1$ and velocity $V_2$ can each be independently determined as described with reference to FIG. 18, since beams 332 and 334 are same-direction beams and beams 344 and 346 are also same-direction beams. If, as shown in FIG. 20B, axis 338 and axis 340 are perpendicular, v is equal to.

$$v = \sqrt{V_1^2 + V_2^2} \quad (32)$$

However, if the projection axes are not perpendicular, V can still be calculated from its two linearly independent projections VI and V, since the angle between the projections can be determined from the geometry of transducer 330.

In one embodiment of the invention, the diameter of the aorta is determined by measuring the time delay of pulses reflected from the aortic vessel wails. In a preferred embodiment of the invention, an inner diameter of the aorta is determined. This is possible, for example, if the velocity of flow 22 in the aorta is determined using a pulse-Doppler wave sequence. Reflections from inside the aorta will have a Doppler-shift, while reflections from outside the Aorta will not. Reflections from the aortic walls will have a much lower Doppler-shift than reflections from the blood, albeit with a higher amplitude. The determined diameter of the aorta is actually a projection of the circular-cross-section of the aorta. This projection can be corrected since the incidence angle of the ultrasonic beams is known, and the flow direction is along the main axis of the aorta. In cases where the direction of the flow is not alone the main axis of the aorta, the incidence angle to the aorta can be determined using two of beams 332, 334 and 336, as described herein. Preferably, diameter changes are determined along all three beams, so they can be synchronized to the pulse wave.

The flow-volume is determined from the flow velocity and the diameter. The stroke volume can be estimated by integrating he flow-volume over time. It should be noted the pulse wave, which is determined, corresponds to the cardiac cycle.

FIG. 20C shows a preferred configuration for transducer 330, which can be constructed by trisecting a circular disk of piezoelectric material.

Figure 21:
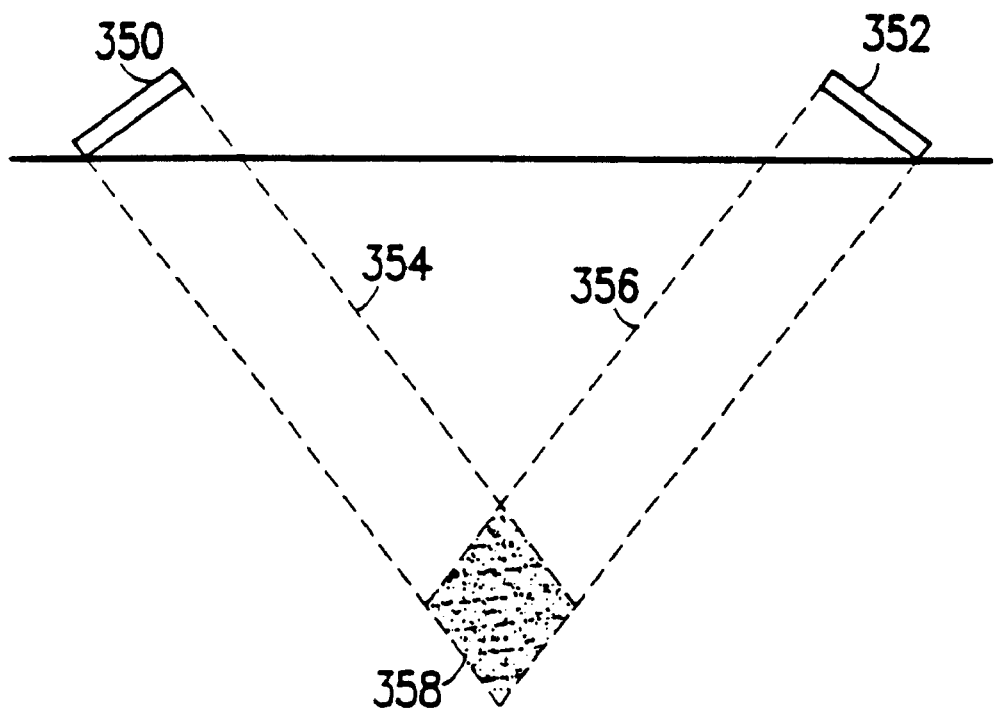
FIG. 21 is a schematic diagram showing a method of determining a perfusion of a tissue portion.

A Doppler-ultrasound device for analyzing microcirculation is disclosed in "Design for an Ultrasound-Based Instrument for Measurement of Tissue Blood Flow", by Burns, S. M. and Reid. M. H. in *Biomaterials, Artificial Cells and Artificial Organs*, Volume 17, Issue 1 page 61–68, 1989, the disclosure of which is incorporated herein by reference. FIG. 21 is a schematic side view of a tissue portion 358 which lies at an intersection of two ultrasonic beams 354 and 356. Doppler-shifted reflections from beams 354 and 356 are summed, and preferably depth gated, so that only reflections from portion 358 are processed. Alternatively, other embodiments of the present invention, such as shown in FIG. 11A or FIG. 19B are used for determining the flow velocity in tissue portion 358. The amplitude of the summed Doppler spectrum is indicative of the amount of flow, while the maximum extent of the spectrum is indicative of the lumen of the largest artery in portion 358.

Figure 22A:
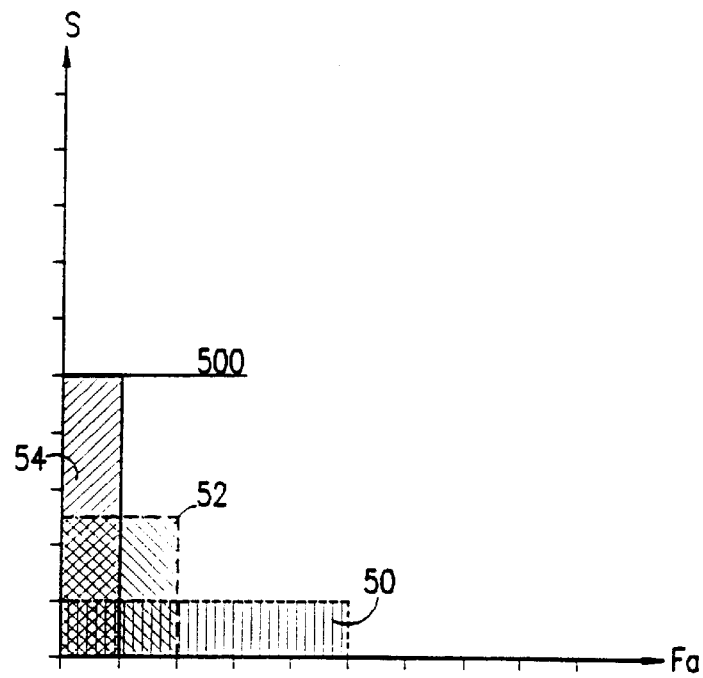
FIG. 22A and 22B are schematic graphs showing intensities of detectable gas bubbles with and without processing according to a preferred embodiment of the invention.
Figure 22B:
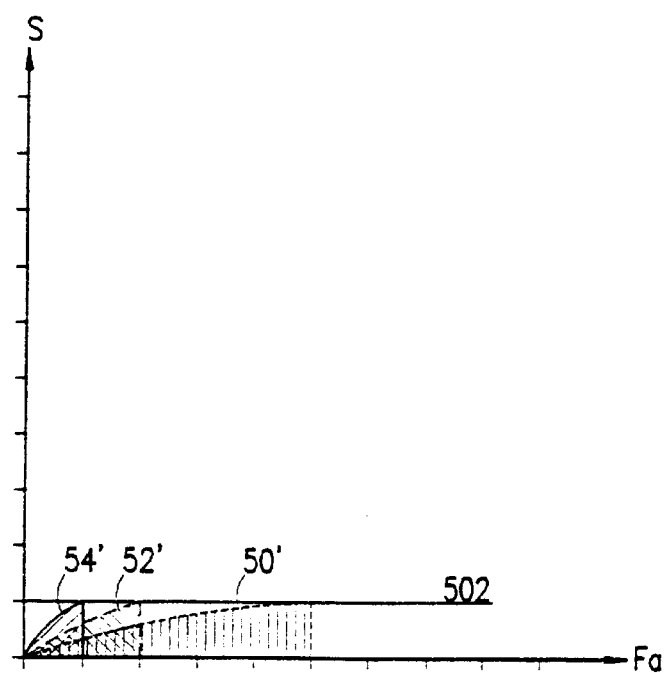

Another aspect of the invention relates to detecting gas bubbles in the blood. Gas bubbles may be found in the blood as a result of trauma, decompression illness and medical procedures which independently circulate the blood, such as CPB, and perhaps dialysis. A gas bubble may be detected using Doppler-ultrasound because the intensity of the reflection from a gas bubble is many times the intensity of a reflection from a red blood cell. FIG. 22A illuminates a main limitation to the sensitivity of detecting gas bubbles using regular Doppler-ultrasound. FIG. 22A, which is similar to FIG. 3A shows a plurality of Doppler-shifted spectra 50,52 and 54, all of which are the Doppler-shifted reflections of a single vessel, at different times in the cardiac cycle. The maximum amplitude of the Doppler-shifted spectra is always changing, so it is difficult to detect gas bubbles which have a reflection whose intensity is less than that indicated by a line 500. FIG. 22B, which is similar to FIG. 3B, shows the effect of filtering a Doppler-shifted spectrum in a frequency-dependent manner according to a preferred embodiment of the invention. Since the maximum amplitude of the processed spectrum is substantially constant, it is easy to detect gas bubble whose reflection intensity is as low as indicated by a line 502 which is much lower than line 500 and which is the same amount for all frequencies. Alternatively, instead of filtering the Doppler spectrum in a frequency dependent manner, it is possible to compare the Doppler spectrum against a frequency-dependent threshold. It should be appreciated, that filtering the spectrum and comparing it to a constant threshold can usually be done using a simpler hardware design than comparing the spectrum to a non-constant threshold.

Figure 23:
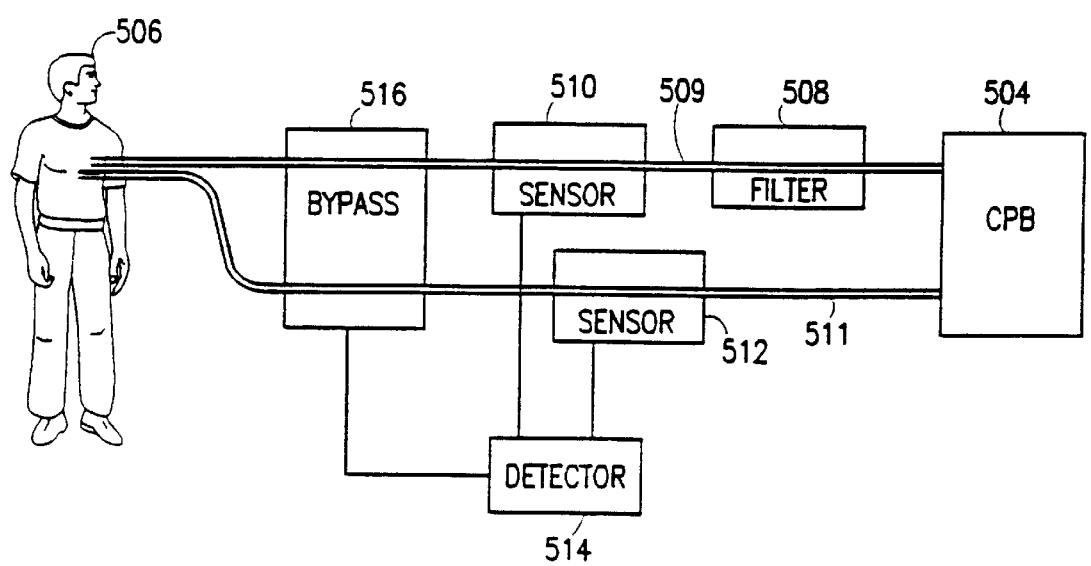
FIG. 23 is a schematic diagram of a CPB (cardiopulmonary bypass) incorporating a gas bubble detector according to a preferred embodiment of the invention.

FIG. 23 shows a CPB device 504, which circulates and oxygenates the blood of a patient 506. Typically, a filter 508 is used to remove gas bubble from the blood of patient 506. In a preferred embodiment of the invention, a sensor 3)10 of a bubble detector 514 is mounted on a tube 509 through which oxygenated blood flows. Additionally or alternatively, a sensor 512 is mounted on a tube 511 through which venous blood flows. Optionally, detector 514 may activate a bypass 516 to prevent an especially large bubble from entering the circulatory system of patient 506.

Figure 24A:
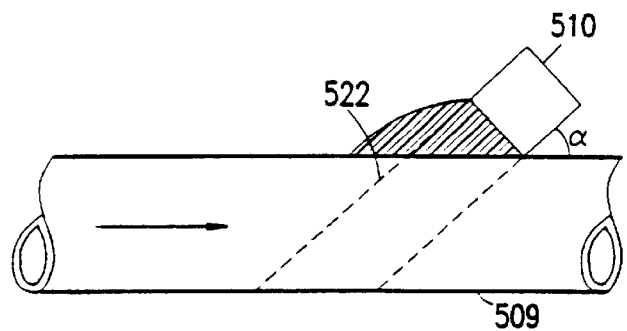
FIG. 24A is a schematic side view of an ultrasonic sensor mounted on a blood carrying tube of the CPB of FIG. 23.

FIG. 24A is a schematic side view of sensor 510 which is mounted on tube 509. Sensor 510 transmits an ultrasonic beam towards tube 509 and detects the Doppler-shifted reflection from red blood cells and gas bubbles. It should be noted that since the incidence angle of beam 522 can be known precisely, there is no need to use a two-directional sensor, such as shown in FIG. 1A.

Figure 24B:
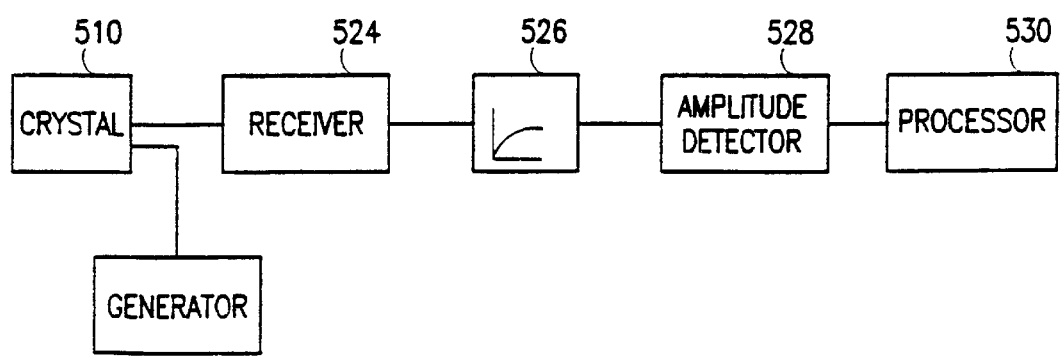
FIG. 24B is a schematic diagram of a gas bubble detector circuit according to a preferred embodiment of the invention.

FIG. 24B shows a schematic diagram of a circuit for detecting gas bubbles according to a preferred embodiment of the invention. A signal is received from sensor 510 by a receiver 524. A filter 526 filters the signal in a frequency dependent manner, with the effect of reducing the variance of the amplitude of the signal from the blood. Then, a simple limit detector 528 detects gas bubbles as signals which are more intense than an allowed signal intensity. An optional processor 530 may be used to further process the signal and/or act upon detected bubbles, such as activating an alarm.

Figure 25A:
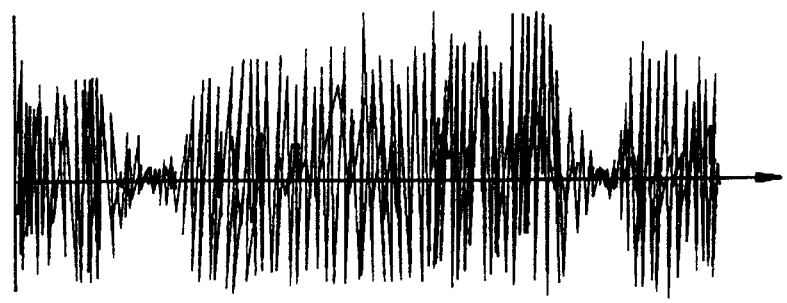
FIGS. 25A–F are graphs showing various processed and unprocessed spectra which may be acquired by the gas bubble detector of FIG. 23.
Figure 25B:
Figure 25C:
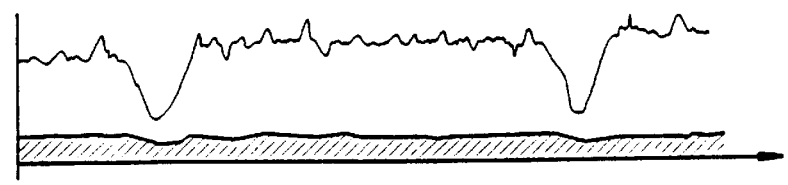
Figure 25D:
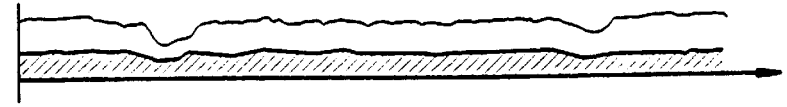

FIGS. 25A–25F show Doppler-shifted signals in the time domain as might be acquired by sensors 510 and 512. FIG. 25A is an unprocessed Doppler-shifted signal of blood without gas bubbles, where unprocessed and processed referred to filtration in a frequency-dependent manner according to a preferred embodiment of the present invention. FIG. 25B is the signal of FIG. 25A after filtration and maximum amplitude detection. It should be noted that signal of FIG. 25B is substantially flat, indicating a substantially uniform peak velocity (and no reflections from air bubbles). FIG. 25C shows the signal of FIG. 25B in comparison with a processed signal of blood which is oxygenated by CPB 504, such as might be acquired by sensor 510. The difference in amplitude reflects the number and size of gas bubbles in the blood. FIG. 25D shows the signal of FIG. 25B in comparison with a processed signal of venous blood before it enters CPB 504, such as might be acquired by sensor 512. The difference in amplitudes between FIGS. 25C and 25D is due to the absorption and filtration of some of the gas bubbles by patient 506.

Figure 25E:
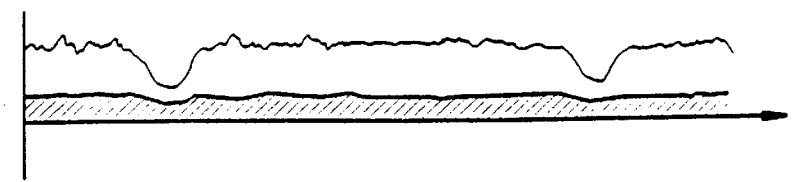
Figure 25F:
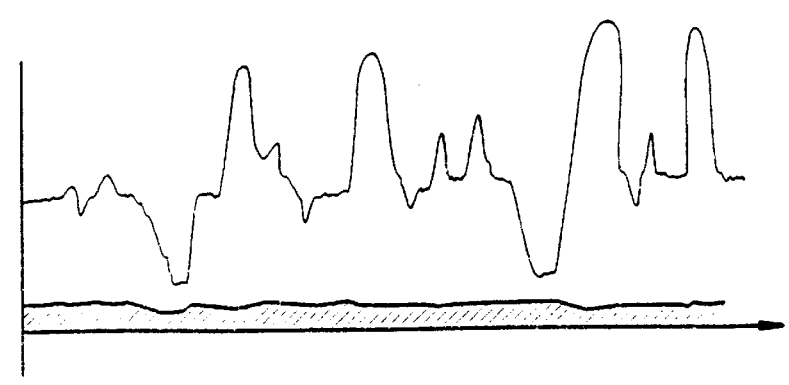

In open heart surgery, patient 506 is usually cooled to reduce his oxygen requirements. Fast warning of patient 506, such as by warning he blood, may cause gas bubbles to form and grow in patient 506. FIG. 25E shows the effect of fast warming on the amplitude changes which indicate gas bubbles FIG. 25F shows the effect of removing bubble filter 508.

Monitoring is important for deep sea divers and spacemen who undergo many compression/decompression cycles. A preferred embodiment of the invention provides a personal gas-bubble monitor. Such a monitor comprises at least one ultrasonic transducer to determine a Doppler-shifted spectrum of a blood vessel, preferably more than one ultrasonic transducer is used, such as described above with respect to FIG. 1C. A bubble detector circuit, such as shown in FIG. 24B is used to detected gas bubbles in the signal. In one preferred embodiment of the invention the monitor has an alarm to indicate the presence of bubbles to the user. Alternatively, the monitor is connected to a computer, such as a diving computer, so that a more comprehensive picture of bubble exposure can be determined. The personal monitor is preferably located on the chest so that a major vein can be monitored. Alternatively, the monitor is worn on a wrist like a wristwatch, with the ultrasonic transducer on the inside of the wrist.

It will be appreciated by persons skilled in the art that the present invention is not limited to what has thus far been described. Rather the scope of the present invention is limited only by the claims which follow.

What is claimed is:

1. A method for determining a flow velocity of a flowing material suspended in a liquid and flowing in a conduit, comprising:

irradiating the conduit with ultrasonic waves, wherein the conduit is a blood vessel;

detecting first Doppler-shifted reflections of the waves from the flowing material, wherein the first Doppler-shifted reflections have a positive Doppler-shift;

detecting second Doppler-shifted reflections of the waves from the flowing material, wherein the second Doppler-shifted reflections have a negative Doppler-shift;

filtering at least one of the first and second reflections to provide a peak signal-amplitude, wherein the peak signal amplitude is substantially velocity independent to provide first and second reflection signals;

generating a composite signal using the first and second reflection signals; and estimating the flow velocity as a function of the composite signal.

2. The method according to claim 1, wherein the step of generating the composite signal comprises combining the first and second Doppler-shifted reflection signals to form the composite signal, and wherein the step of estimating the flow velocity comprises determining a range of Doppler-shifts in the composite signal.

3. The method according to claim 1, wherein the step of generating a composite signal comprises summing a spectra of the first and second Doppler-shifted reflection signals to form a composite spectrum.

4. The method according to claim 1, wherein the estimation of the flow velocity comprises:

determining a maximum velocity of a flow; and determining a flow-average velocity of the flow as a function of the determined maximum velocity.

5. The method according to claim 1, wherein the estimation of the flow velocity comprises:

determining a quadric-average velocity of a flow; and determining a flow-average velocity of the flow as a function of the determined quadric-average velocity.

6. The method according to claim 1, wherein the estimation of the flow velocity comprises:

determining a relative attenuation between the first Doppler-shifted reflections and the second Doppler-shifted reflections;

determining a first travel time of the first Doppler-shifted reflections from the flowing material to a first detector;

determining a second travel time of the second Doppler-shifted reflections from the material to a second detector; and determining an attenuation-per-unit length of the first and second Doppler-shifted reflections as a function of the determined first and second travel times and of the determined relative attenuation.

7. The method according to claim 6, further comprising:

determining a first angle between the first Doppler-shifted reflections and a flow direction of the material as a function of the determined first and second travel times.

8. The method according to claim 7, wherein a flow has a substantially circular cross-section, and further comprising:

determining a diameter of one of the flowing material and the conduit; and correcting the diameter as a function of the first angle.

9. The method according to claim 6, further comprising:

converting the first and second travel times to distances as a function of a measured velocity of ultrasound waves in a soft tissue surrounding the flowing material.

10. The method according to claim 1, wherein a flow of the flowing material has a pulse, and further comprising:

determining a first particular phase of the pulse of the flow of the first Doppler-shifted reflections;

determining a time delay to provide a second particular phase for the second Doppler-shifted reflections; and delaying a signal generated by one of the first and second Doppler-shifted reflections as a function of the time delay.

11. The method according to claim 10, wherein the step of determining the first particular phase comprises determining the first particular phase from changes in a diameter of the conduit.

12. The method according to claim 11, wherein the changes in the diameter are determined using ultrasonic sensors.

13. The method according to claim 11, wherein the step of determining the first particular phase comprises determining the first particular phase as a function of reflections from the conduit.

14. The method according to claim 10, wherein the step of determining the first particular phase comprises determining the first particular phase as a function of the first Doppler-shifted reflections from the flowing material.

15. A method for determining a pressure exerted by a flowing material on a conduit, comprising:

irradiating the conduit with ultrasonic waves, wherein the conduit is a blood vessel;

detecting first Doppler-shifted reflections of the waves from the flowing material, wherein the first Doppler-shifted reflections have a positive Doppler-shift;

detecting second Doppler-shifted reflections of the waves from the flowing material, wherein the second Doppler-shifted reflections have a negative Doppler-shift;

filtering at least one of the first and second reflections to have a peak signal-amplitude, wherein the peak signal amplitude is substantially velocity independent;

generating a composite signal using the first and second reflections;

estimating a flow velocity of the flowing material as a function of the composite signal;

determining a cross-section of the conduit;

determining an equivalent length of the conduit; and determining the pressure as a function of the determined cross-section of the conduit, the determined equivalent length and the estimated flow velocity.

16. The method according to claim 15, wherein a flow of the flowing material has a pulse wave, and wherein the determination of the equivalent length comprises:

determining a velocity of the pulse wave;

determining a travel time of the pulse wave along the conduit; and determining the equivalent length as a function of the determined pulse wave velocity and the determined travel time.

17. The method according to claim 15, wherein the blood pressure determination comprises non-invasively determining a time-dependent blood pressure at a first location on a body and repeating the non-invasively determination of the time-dependent blood pressure at a plurality of locations.

18. The method according to claim 17, wherein the non-invasively determination of the time-dependent blood pressure comprises non-invasively determining a local blood pressure only as a function of local measurements.

19. The method according to claim 15, further comprising:

non-invasively determining a first local blood pressure at a first location;

non-invasively determining a second local blood pressure at a second location; and comparing the first and second local blood pressures to determine the presence of a stenosis.

20. A method for non-invasively determining a local blood pressure at a location of a blood vessel in a circulatory system, the circulatory system coupled at one end by a heart and at a capillary end by capillaries, the blood vessel allowing a flowing material to flow therethrough, the method comprising:

determining a local impedance to a flow of blood in the blood vessel;

determining an end impedance to the flow of the blood at the capillary end of the circulatory system;

irradiating the blood vessel with ultrasonic waves;

detecting first Doppler-shifted reflections of the waves from the flowing material, wherein the first Doppler-shifted reflections have a positive Doppler-shift;

detecting second Doppler-shifted reflections of the waves from the flowing material, wherein the second Doppler-shifted reflections have a negative Doppler-shift;

filtering at least one of the first and second reflections to have a peak signal-amplitude, wherein the peak signal amplitude is substantially velocity independent;

generating a composite signal using the first and second reflections;

estimating a flow velocity of the flowing material as a function of the composite signal;

determining a blood flow volume as a function of the estimated flow velocity; and determining an instantaneous local blood pressure at the location of the blood vessel as a function of the determined local impedance, the determined end impedance and the determined blood flow volume.

21. The method according to claim 20, further comprising:

determining a reflectance at the capillary end; and determining the local and end impedances as a function of the determined reflectance.

22. The method according to claim 21, further comprising:

determining a complex value of the reflectance by measuring an amplitude and a phase of reflected pulse waves.

23. The method according to claim 21, wherein the step of determining the reflectance comprises:

determining the reflectance before the capillaries are dilated; and determining a further reflectance after the capillaries are dilated.

* * * * *